United States Patent
Kuhn et al.

(10) Patent No.: US 12,054,518 B2
(45) Date of Patent: Aug. 6, 2024

(54) ANTIMICROBIAL PEPTIDES AND METHODS OF USING SAME

(71) Applicant: Zoetis Services LLC, Parsippany, NJ (US)

(72) Inventors: Michael Kuhn, Kalamazoo, MI (US); Christopher A. Zook, Kalamazoo, MI (US); Derek James Sheehan, Galesburg, MI (US); Eric Baima, Kalamazoo, MI (US); Richard Andrew Ewin, Kalamazoo, MI (US); Hilary Phelps, Jackson, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 17/738,572

(22) Filed: May 6, 2022

(65) Prior Publication Data

US 2023/0077604 A1     Mar. 16, 2023

Related U.S. Application Data

(63) Continuation of application No. 16/769,025, filed as application No. PCT/US2018/064029 on Dec. 5, 2018, now Pat. No. 11,352,396.

(60) Provisional application No. 62/595,725, filed on Dec. 7, 2017.

(51) Int. Cl.
| | |
|---|---|
| *C07K 14/00* | (2006.01) |
| *A61K 38/00* | (2006.01) |
| *A61P 31/04* | (2006.01) |
| *C07K 7/08* | (2006.01) |

(52) U.S. Cl.
CPC ............ *C07K 14/001* (2013.01); *A61K 38/00* (2013.01); *A61P 31/04* (2018.01); *C07K 7/08* (2013.01)

(58) Field of Classification Search
CPC ............................ C07K 14/001; A61K 38/00
See application file for complete search history.

(56) References Cited

PUBLICATIONS

Schaefer et al., 2012, Acute Otitis Externa: An Update, Am Fam Physician, 86(11): 1055-1061.*
Giroir et al., 2001, Bactericidal/Permeability-Increasing Protein: Clinical Development and Potential Pediatric Applications, Pediatr Infect Dis, 20(9): 885-887.*
Voget et al., 2015, Is transmission electron microscopy (TEM) a promising approach for qualitative and quantitative investigations of polymyxin B and miconazole interactions with cellular and subcellular structures of *Staphylococcus pseudintermedius, Escherichia coli*, . . . , Veterinary Microbiology, 181: 261-270.*
Pietschmann et al., 2013, The joint in vitro action of polymyxin B and miconazole against pathogens associated with canine otitis externa from three European countries, Vet Dermatol, 24: 439445 and e96-e97.*

* cited by examiner

*Primary Examiner* — Amber D Steele
(74) *Attorney, Agent, or Firm* — Vyacheslav Vasilyev

(57) ABSTRACT

Antimicrobial peptides of general formula $X_0X_1X_2CX_3X_4X_5CX_6X_7X_8X_9CYX_{10}X_{11}CX_{12}X_{13}$ (SEQ ID NO: 12) are provided. Also provided are certain formulations containing these peptides and methods of using these peptides for treating skin infections in an animal in need thereof.

18 Claims, 1 Drawing Sheet
Specification includes a Sequence Listing.

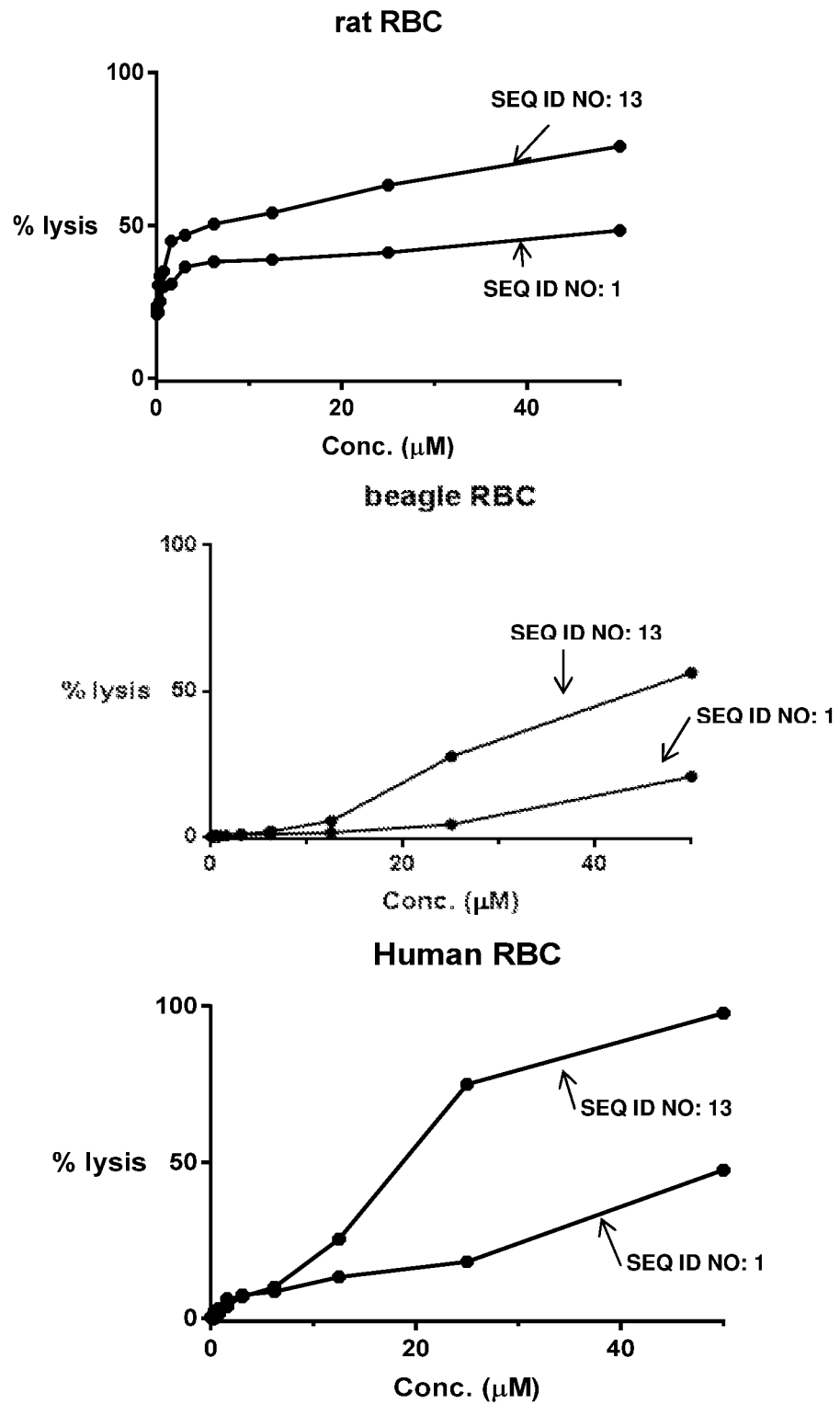

ANTIMICROBIAL PEPTIDES AND METHODS OF USING SAME

CROSS-REFERENCE TO RELATED APPLICATIONS

This application is a continuation of U.S. application Ser. No. 16/769,025 filed on Jun. 2, 2020, now U.S. Pat. No. 11,352,396, which is a National Stage of PCT Application PCT/US2018/064029 filed on Dec. 5, 2018, which is a non-provisional application of U.S. Provisional Application Ser. No. 62/595,725 filed Dec. 7, 2017.

FIELD OF THE INVENTION

This invention is in the field of antimicrobial peptides and uses of such peptides for treatment of infections.

BACKGROUND

Antibiotics are chemical substances having the capacity, in a dilute solution, to kill or inhibit growth of microorganisms. Antibiotics that are sufficiently nontoxic to the host are used as chemotherapeutic agents to treat infectious diseases of humans, animals, and plants. The term was originally restricted to substances produced by microorganisms, but has been extended to include synthetic and semi-synthetic compounds of similar chemical activity.

Extensive and widespread use of antimicrobial drugs led to the emergence of resistant strains of microorganisms. These microorganisms are no longer susceptible to currently available antimicrobial drugs. In order to lower or prevent lethal infectious diseases and maintain public health, new antimicrobial agents are required.

Antimicrobial Peptides (AMPs) are an essential component of the host defense system of organisms throughout nature and offer protection from invading pathogens. They show potent antimicrobial activity against Gram-positive and Gram-negative bacteria, fungi, parasites and viruses. The smaller AMPs (usually about 15-40 amino acids) act largely by disrupting the structure or function of microbial cell membranes, they do not target single defined molecular structures. Therefore, as opposed to conventional antibiotics, they are effective regardless of the metabolic activity of bacteria. Human AMPs such as defensins and cathelicidin (LL-37) are present in leukocytes and secreted by various epithelia in skin and mucosal surfaces. In addition to their antimicrobial activity, AMPs are important effector molecules in inflammation, immune activation, and wound healing. AMPs are quite diverse in sequence and secondary structure, but share some common properties. They are usually cationic, amphipathic and exert their microbicidal effect by compromising the bacterial membrane integrity. Interaction of AMPs with the anionic membrane surface of the target microbes leads to membrane permeabilization, cell lysis and death.

SUMMARY OF INVENTION

In the first aspect, the invention provides an amino acid sequence of 17-22 amino acids long and comprising, at its N-terminus, SEQ ID NO:12 ($X_0X_1X_2CX_3X_4X_5CX_6X_7X_8X_9CYX_{10}X_{11}CX_{12}X_{13}$) wherein $X_0$ is absent or proline; $X_1$ is lysine, arginine, glycine, or proline; $X_2$ is phenylalanine, tryptophan, or arginine; $X_3$ is phenylalanine, valine or tryptophan; $X_4$ is arginine, tyrosine or phenylalanine; $X_5$ is valine or alanine; $X_6$ is tyrosine or arginine or lysine or tryptophan; $X_7$ is arginine, phenylalanine, or glycine; $X_8$ is arginine, phenylalanine or glycine; $X_9$ is isoleucine, alanine, phenylalanine, tyrosine or valine; $X_{10}$ is arginine or histidine; $X_{11}$ is arginine or lysine; $X_{12}$ is arginine, lysine, or asparagine; $X_{13}$ is a 0-4 amino-acid-long polypeptide; with provisos that if $X_0$ is proline, then $X_1$ is not proline; if said amino acid sequence comprises SEQ ID NO: 13 (KWCFRVCYRGI-CYRRCR), or SEQ ID NO: 28 (KWCFRVCYRGI-CYRKCR) then $X_{13}$ is 1-4 amino acids long; if $X_{13}$ is 1 amino acid long or longer, then the N-terminal amino acid in $X_{13}$ is aspartic acid or glutamic acid; if the amino acid at position corresponding to position 1 of SEQ ID NO: 1 is glycine, then said glycine is not acyl- or palmitic acid—modified; if amino acid is $X_{11}$ lysine then $X_6X_7X_8X_9$ (SEQ ID NO: 14) is not RRRF (SEQ ID NO: 15); and if the amino acid is GFCWYVCYRGICYRRCN (SEQ ID NO: 16) then the C-terminal asparagine is amidated.

In certain embodiments, $X_0$ is absent and $X_6$ is arginine or lysine; and/or $X_7$ is arginine or lysine; $X_6X_7X_8X_9$(SEQ ID NO: 14) is selected from the group consisting of YRGI (SEQ ID NO: 17), YRGV (SEQ ID NO: 18), YRGF (SEQ ID NO: 19); and/or $X_{10}$ is arginine; and/or $X_3X_4X_5$ (SEQ ID NO: 20) is FRV (SEQ ID NO: 21), WYV (SEQ ID NO: 22); and/or $X_{13}$ is 1 amino acid long or longer, and the N-terminal amino acid in $X_{13}$ is aspartic acid.

In a particular set of embodiments, the amino acid sequence is 17-21 amino acids long and comprises, at its N-terminus, SEQ ID NO:12 ($X_0X_1X_2CX_3X_4X_5CX_6X_7X_8X_9CYX_{10}X_{11}CX_{12}X_{13}$) wherein $X_0$ is absent; $X_1$ is lysine, arginine or glycine; $X_2$ is phenylalanine, tryptophan, or arginine; $X_3$ is phenylalanine, valine or tryptophan; $X_4$ is tyrosine or phenylalanine; $X_5$ is valine or alanine; $X_6$ is tyrosine or arginine; $X_7$ is arginine or glycine; $X_8$ is arginine, phenylalanine or glycine; $X_9$ is alanine, phenylalanine, tyrosine or valine; $X_{10}$ is arginine or histidine; $X_{11}$ is arginine or lysine $X_{12}$ is arginine, lysine, or asparagine; $X_{13}$ is a 0-4 amino-acid-long polypeptide.

In a another set of embodiments according to the first aspect, the amino acid sequence is 18-21 amino acids long and comprises, at its N-terminus, SEQ ID NO: 1 (KWCFRVCYRGICYRRCRD) or a peptide that differs from SEQ ID NO: 1 by one, two, three, or four amino acids, wherein the amino acids differing from the amino acids of SEQ ID NO: 1 are independently selected from the group consisting of arginine or glycine at position corresponding to position 1 of SEQ ID NO: 1; phenylalanine or arginine at position corresponding to position 2 of SEQ ID NO: 1; valine or tryptophan at position corresponding to position 4 of SEQ ID NO: 1; tyrosine at position corresponding to position 5 of SEQ ID NO: 1; arginine at position corresponding to position 8 of SEQ ID NO: 1; glycine at position corresponding to position 9 of SEQ ID NO: 1; arginine at position corresponding to position 10 of SEQ ID NO: 1; alanine, phenylalanine, or valine at position corresponding to position 11 of SEQ ID NO: 1; histidine at position corresponding to position 14 of SEQ ID NO: 1; lysine at position corresponding to position 15 of SEQ ID NO: 1; asparagine at position corresponding to position 17 of SEQ ID NO: 1.

More specifically, the amino acid sequence comprises aspartic acid at position corresponding to position 18 of SEQ ID NO: 1; and/or asparagine at position corresponding to position 17 of SEQ ID NO: 1; and/or glycine at position corresponding to position 1 of SEQ ID NO: 1; alanine at position corresponding to position 11 of SEQ ID NO: 1;

and/or arginine at position corresponding to position 14 of SEQ ID NO: 1, at position corresponding to position 15 of SEQ ID NO: 1, or both.

In a set of embodiments, the amino acid sequence is selected from the group consisting of amino acid sequences comprising, at the respective N-termini, SEQ ID NO: 1, SEQ ID NO: 2 (RWCFRVCYRGICYRRCRD), SEQ ID NO: 3 (GWCFRVCYRGICYRRCRD), SEQ ID NO: 4 (KFCFRVCYRGICYRRCRD); SEQ ID NO: 5 (KWCFYVCYRGICYRRCRD), SEQ ID NO: 6 (KWCFRVCRRGICYRRCRD), SEQ ID NO: 7 (KWCFRVCYRGVCYRRCRD), SEQ ID NO: 8 (KWCFRVCYRGACYRRCRD), SEQ ID NO: 9 (KWCFRVCYRGFCYRRCRD), SEQ ID NO: 10 (KWCFRVCYRGICYHRCRD), or SEQ ID NO: 11 (KWCFRVCYRGICYRRCND).

In additional embodiments, the amino acid sequence is selected from the group consisting of SEQ ID NO: 97 (KRCFRVCYRGICYRRCRD); SEQ ID NO: 98 (KWCVRVCYRGICYRRCRD), SEQ ID NO: 99 (KWCFFVCYRGICYRRCRD), SEQ ID NO: 100 (KWCFWVCYRGICYRRCRD), SEQ ID NO: 102 (KWCFRACYRGICYRRCRD), SEQ ID NO: 104 (KWCFRVCYFGICYRRCRD), SEQ ID NO: 105 (KWCFRVCYRGICYRRCRN), SEQ ID NO: 106 (KWCWRVCYRGICYRRCRD), SEQ ID NO: 107 (KWCFRVCWRGICYRRCRD), SEQ ID NO: 108 (KWCFRVCYGGICYRRCRD), SEQ ID NO: 109 (KWCFRVCYRRICYRRCRD), SEQ ID NO: 110 (KWCFRVCYRGYCYRRCRD), SEQ ID NO: 112 (KWCFRVCYRGICYRRCKD), SEQ ID NO: 113 (KWCFRVCYRGICYRRCAD), SEQ ID NO: 114 (KWCFRVCYRGICYRRCRR), SEQ ID NO: 115 (GWCFRVCYRGICYRRCND), SEQ ID NO: 116 (KWCFYVCYRGICYRRCND), SEQ ID NO: 117 (GWCFYVCYRGICYRRCRD), SEQ ID NO: 32 (GWCFYVCYRGICYRRCND).

In yet additional embodiments, the amino acid sequence is selected from the group consisting of SEQ ID NO: 28, 29, 30, 31.

In the second aspect, the invention provides a multimer comprising a plurality of repeats of the amino acid sequence according to the previous aspect of the invention, wherein further, the N-terminal amino acid of said sequence is proline, and the C-terminal amino acid of said sequence is aspartic acid. Advantageously, the repeats of the amino acid sequence are joined each other directly, thereby forming D-P bonds. In certain embodiments, the plurality is between 2 and 20.

The invention also provides a method of making the amino acid sequence that is suitable for making the multimer as described in the second aspect of the invention. The method comprises synthesizing the multimer and contacting the multimer with a mild acid (e.g., formic acid) whereby D-P bonds are broken.

In a third aspect, the invention provides a method of treating infections in an animal in need thereof, comprising administering to the animal a formulation comprising the amino acid sequence according to the first aspect of the invention. In certain embodiments, the infection is a skin infection. In other embodiments, the infection is mastitis, a respiratory infection, an ear infection, urinary tract infection, or reproductive tract infection.

In certain embodiments, the animal is a companion animal, e.g., a dog, a cat, or a horse. In a particular embodiment, the animal is a dog. In certain embodiments, the formulation is formulated for a topical application. In some embodiments, the formulation is a gel, a cream, an emulsion, or a spray.

BRIEF DESCRIPTION OF THE DRAWINGS

FIG. 1 illustrates toxicity of SEQ ID NOs: 1 and 13 in human, beagle, and rat red blood cells.

DETAILED DESCRIPTION

Definitions

For a better understanding of the invention, the following non-limiting definitions are provided:

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Emulsion" means a composition of two immiscible liquids in which small droplets of one liquid are suspended in a continuous phase of the other liquid.

"Parenteral administration" refers to the introduction of a substance, such as a vaccine, into a subject's body through or by way of a route that does not include the digestive tract. "Parenteral administration" includes subcutaneous, intramuscular, transcutaneous, intradermal, intraperitoneal, intraocular, and intravenous administration.

"Position [in a sequence of interest] corresponding to" a certain position of a reference sequence is determined by aligning the reference sequence and the sequence of interest in such a way that the cysteine residues of the sequence of interest and the reference sequence are matched to each other, and then determining the position in the sequence of interest that matcher the desired position in the reference sequence.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"Therapeutically effective amount" refers to an amount of the amino acid sequence and/or the formulation containing same that would induce a response in a subject receiving the amino acid or formulation which is adequate to prevent or reduce signs or symptoms of infection.

"Treating" refers to preventing a disorder, condition, or disease, including, without limitations, infections, to which such term applies, or to preventing or reducing one or more symptoms of such disorder, condition, or disease.

"Treatment" refers to the act of "treating" as defined above.

Peptides

Generally, the invention provides an amino acid sequence of 17-22 amino acids long and comprising, at its N-terminus, SEQ ID NO:12 $(X_0X_1X_2CX_3X_4X_5CX_6X_7X_8X_9CYX_{10}X_{11}CX_{12}X_{13})$ wherein $X_0$ is absent or proline;

$X_1$ is lysine, arginine, glycine, or proline;

$X_2$ is phenylalanine, tryptophan, or arginine;

$X_3$ is phenylalanine, valine or tryptophan;

$X_4$ is arginine, tyrosine or phenylalanine;
$X_5$ is valine or alanine;
$X_6$ is tyrosine or arginine;
$X_7$ is arginine, phenylalanine, or glycine;
$X_8$ is arginine, phenylalanine or glycine;
$X_9$ is isoleucine, alanine, phenylalanine, tyrosine or valine;
$X_{10}$ is arginine or histidine;
$X_{11}$ is arginine or lysine;
$X_{12}$ is arginine, lysine, or asparagine;
$X_{13}$ is a 0-4 amino-acid-long polypeptide;
with provisos that if $X_0$ is proline, then $X_1$ is not proline; if said amino acid sequence comprises SEQ ID NO: 13 (KWCFRVCYRGICYRRCR), or SEQ ID NO: 28 (KWCFRVCYRGICYRKCR) then $X_{13}$ is 1-4 amino acids long; if $X_{13}$ is 1 amino acid long or longer, then the N-terminal amino acid in $X_{13}$ is aspartic acid or glutamic acid; if the amino acid at position corresponding to position 1 of SEQ ID NO: 1 is glycine, then said glycine is not acyl- or palmitic acid—modified; if amino acid is $X_{11}$ lysine then $X_6X_7X_8X_9$ (SEQ ID NO: 14) is not RRRF (SEQ ID NO: 15); and if the amino acid is GFCWYVCYRGICYRRCN (SQE ID NO: 16) then the C-terminal asparagine is amidated.

In certain embodiments, $X_0$ is absent and $X_6$ is arginine or lysine; and/or $X_7$ is arginine or lysine; $X_6X_7X_8X_9$ (SEQ ID NO: 14) is selected from the group consisting of YRGI (SEQ ID NO: 17), YRGV (SEQ ID NO: 18), YRGF (SEQ ID NO: 19); and/or $X_{10}$ is arginine; and/or $X_3X_4X_5$ (SEQ ID NO: 20) is FRV (SEQ ID NO: 21), WYV (SEQ ID NO: 22); and/or $X_{13}$ is 1 amino acid long or longer (e.g., 1, 2, 3, or 4 amino acids long), and the N-terminal amino acid in $X_{13}$ is aspartic acid.

In a particular set of embodiments according to the first aspect, the amino acid sequence is 18-21 amino acids long and comprises, at its N-terminus, SEQ ID NO: 1 (KWCFRVCYRGICYRRCRD) or a peptide that differs from SEQ ID NO: 1 by one, two, three, or four amino acids, wherein the amino acids differing from the amino acids of SEQ ID NO: 1 are independently selected from the group consisting of arginine or glycine at position corresponding to position 1 of SEQ ID NO: 1; phenylalanine or arginine at position corresponding to position 2 of SEQ ID NO: 1; valine or tryptophan at position corresponding to position 4 of SEQ ID NO: 1; tyrosine at position corresponding to position 5 of SEQ ID NO: 1; arginine at position corresponding to position 8 of SEQ ID NO: 1; glycine at position corresponding to position 9 of SEQ ID NO: 1; arginine at position corresponding to position 10 of SEQ ID NO: 1; alanine, phenylalanine, or valine at position corresponding to position 11 of SEQ ID NO: 1; histidine at position corresponding to position 14 of SEQ ID NO: 1; lysine at position corresponding to position 15 of SEQ ID NO: 1; asparagine at position corresponding to position 17 of SEQ ID NO: 1.

In different embodiments, the amino acid sequence differs from SEQ ID NO: 1 by one, two, or three amino acids.

In certain embodiments, the amino acid sequence comprises aspartic acid at position corresponding to position 18 of SEQ ID NO: 1; and/or asparagine at position corresponding to position 17 of SEQ ID NO: 1; and/or glycine at position corresponding to position 1 of SEQ ID NO: 1; alanine at position corresponding to position 11 of SEQ ID NO: 1; and/or arginine at position corresponding to position 14 of SEQ ID NO: 1, at position corresponding to position 15 of SEQ ID NO: 1, or both.

In a set of embodiments, the amino acid sequence is selected from the group consisting of amino acid sequences comprising, at the respective N-termini, SEQ ID NO: 1, SEQ ID NO: 2 (RWCFRVCYRGICYRRCRD), SEQ ID NO: 3 (GWCFRVCYRGICYRRCRD), SEQ ID NO: 4 (KFCFRVCYRGICYRRCRD); SEQ ID NO: 5 (KWCFYVCYRGICYRRCRD), SEQ ID NO: 6 (KWCFRVCRRGICYRRCRD), SEQ ID NO: 7 (KWCFRVCYRGVCYRRCRD), SEQ ID NO: 8 (KWCFRVCYRGACYRRCRD), SEQ ID NO: 9 (KWCFRVCYRGFCYRRCRD), SQE ID NO: 10 (KWCFRVCYRGICYHRCRD), or SEQ ID NO: 11 (KWCFRVCYRGICYRRCND).

Additional amino acid sequences may be found among SEQ ID NO: 97 (KRCFRVCYRGICYRRCRD); SEQ ID NO: 98 (KWCVRVCYRGICYRRCRD), SEQ ID NO: 99 (KWCFFVCYRGICYRRCRD), SEQ ID NO: 100 (KWCFWVCYRGICYRRCRD), SEQ ID NO: 101 (KWCFRVYCYRGICYRRCRD), SEQ ID NO: 102 (KWCFRACYRGICYRRCRD), SEQ ID NO: 103 (KWCFRVCKRGICYRRCRD), SEQ ID NO: 104 (KWCFRVCYFGICYRRCRD), SEQ ID NO: 105 (KWCFRVCYRGICYRRCRN), SEQ ID NO: 106 (KWCWRVCYRGICYRRCRD), SEQ ID NO: 107 (KWCFRVCWRGICYRRCRD), SEQ ID NO: 108 (KWCFRVCYGGICYRRCRD), SEQ ID NO: 109 (KWCFRVCYRRICYRRCRD), SEQ ID NO: 110 (KWCFRVCYRGYCYRRCRD), SEQ ID NO: 111 (KWCFRVCYRGICRYRRCRD), SEQ ID NO: 112 (KWCFRVCYRGICYRRCKD), SEQ ID NO: 113 (KWCFRVCYRGICYRRCAD), SEQ ID NO: 114 (KWCFRVCYRGICYRRCRR), SEQ ID NO: 115 (GWCFRVCYRGICYRRCND), SEQ ID NO: 116 (KWCFYVCYRGICYRRCND), SEQ ID NO: 117 (GWCFYVCYRGICYRRCRD), SEQ ID NO: 32 (GWCFYVCYRGICYRRCND).

Thus, the amino acid sequence may be selected from the group consisting of SEQ ID NO: 97 (KRCFRVCYRGICYRRCRD); SEQ ID NO: 98 (KWCVRVCYRGICYRRCRD), SEQ ID NO: 99 (KWCFFVCYRGICYRRCRD), SEQ ID NO: 100 (KWCFWVCYRGICYRRCRD), SEQ ID NO: 102 (KWCFRACYRGICYRRCRD), SEQ ID NO: 104 (KWCFRVCYFGICYRRCRD), SEQ ID NO: 105 (KWCFRVCYRGICYRRCRN), SEQ ID NO: 106 (KWCWRVCYRGICYRRCRD), SEQ ID NO: 107 (KWCFRVCWRGICYRRCRD), SEQ ID NO: 108 (KWCFRVCYGGICYRRCRD), SEQ ID NO: 109 (KWCFRVCYRRICYRRCRD), SEQ ID NO: 110 (KWCFRVCYRGYCYRRCRD), SEQ ID NO: 112 (KWCFRVCYRGICYRRCKD), SEQ ID NO: 113 (KWCFRVCYRGICYRRCAD), SEQ ID NO: 114 (KWCFRVCYRGICYRRCRR), SEQ ID NO: 115 (GWCFRVCYRGICYRRCND), SEQ ID NO: 116 (KWCFYVCYRGICYRRCND), SEQ ID NO: 117 (GWCFYVCYRGICYRRCRD), SEQ ID NO: 32 (GWCFYVCYRGICYRRCND).

The peptides according to the invention can be manufactured by methods that are well-known in the art, including, without limitations, solid-phase peptide synthesis. The peptides may also be synthesized using bioengineering techniques (e.g., fermentation) in fungal, bacterial or eukaryotic systems.

In certain embodiments, where the N-terminal amino acid of the antimicrobial peptide is proline, and the C-terminal amino acid is aspartic acid, the method of manufacturing the anti-microbial peptide may entail synthesizing a multimer of the antimicrobial peptide. In different embodiments, the number of monomers in the multimer may be 1 to about 20, e.g., about 5, about 10, or about 15. Conveniently, the monomers of the antimicrobial peptide would be linked via a peptide bond between the C-terminal aspartic acid of an upstream monomer and the N-terminal proline of the downstream monomer (D-P bond). This D-P bond can conveniently be cleaved via mild acid (e.g., formic or citric acid) hydrolysis. Thus, a molecule encompassed by such description as, for example, (SEQ ID NO: 29)$_n$, or (SEQ ID NO: 31)$_n$, wherein n is an integer between 1 and 20, may be used in the compositions and methods of the invention.

Formulations

The peptides according to the embodiments above may be formulated for delivery to the target site (i.e., the site that is infected or the site that is in danger of being infected due to a wound, irritation, to the like). Without limitation, the sites include skin, eyes, ears, mammary gland, reproductive tract, urinary bladder, nasal and oral cavities. The composition comprising the peptides of the instant invention is formulated depending on the site of interest.

Also provided are compositions that can be prepared by mixing one or more antimicrobial peptides described herein, with pharmaceutically acceptable carriers, excipients, binders, diluents or the like, to treat or ameliorate a variety of bacterial infections. A therapeutically effective dose or amount refers to that amount of one or more compounds described herein sufficient to result in amelioration of symptoms of the infection. The pharmaceutical compositions of the instant invention can be manufactured by methods well known in the art such as conventional granulating, mixing, dissolving, encapsulating, lyophilizing, or emulsifying processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, by topical administration, by transmucosal administration, by rectal administration, or subcutaneous administration as well as intrathecal, intravenous, intramammary, intramuscular, intraperitoneal, intranasal, intraocular or intraventricular injection. The compound or compounds of the instant invention can also be administered in a local fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethylcellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments can be added for identification. Tablets and pills can be further treated with suitable coating materials known in the art.

Liquid dosage forms for oral administration can be in the form of pharmaceutically acceptable emulsions, syrups, elixirs, suspensions, slurries and solutions, which can contain an inactive diluent, such as water. Pharmaceutical formulations can be prepared as liquid suspensions or solutions using a sterile liquid, such as, but not limited to, an oil, water, an alcohol, and combinations of these. Pharmaceutically suitable surfactants, suspending agents, emulsifying agents, can be added for oral or parenteral administration.

As noted above, suspensions can include oils. Such oils include peanut oil, sesame oil, cottonseed oil, corn oil, olive oil and mixtures of oils. Suspension preparation can also contain esters of fatty acids such as ethyl oleate, isopropyl myristate, fatty acid glycerides and acetylated fatty acid glycerides. Suspension formulations can include alcohols, such as, but not limited to, ethanol, isopropyl alcohol, hexadecyl alcohol, glycerol and propylene glycol. Ethers, such as but not limited to, poly (ethyleneglycol), petroleum hydrocarbons such as mineral oil and petrolatum; and water can also be used in suspension formulations.

For certain routes of administration, the pharmaceutical formulations can be a spray or aerosol containing and appropriate solvents and optionally other compounds such as, but not limited to, stabilizers, antimicrobial agents, antioxidants, pH modifiers, surfactants, bioavailability modifiers and combinations of these. A propellant for an aerosol formulation can include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Generally, the oil or fatty acid is non-volatile, including natural or synthetic oils, fatty acids, mono-, di- or tri-glycerides.

For injection, the pharmaceutical formulation can be a powder suitable for reconstitution with an appropriate solution as described above. Examples of these include freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

For rectal administration, the pharmaceutical formulations can be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils can also be employed in the preparation of formulations of the soft gelatin type and suppositories. Water, saline, aqueous dextrose and related sugar solutions, and glycerols can be employed in the preparation of suspension formulations which can also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, and sustained-releasing. Thus, the pharmaceutical formulations can also be formulated for controlled release or for slow release.

The instant compositions can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The composition may also contain anti-pruritic medications, including, without limitations, oclatinib and salts thereof (e.g., APOQUEL® and anti-IL-31 antibodies (e.g., CYTOPOINT™).

The composition can also comprise a steroid or an anti-fungal medicine. Suitable steroids include, without limitations, Betamethasone, triamcinolone acetonide, hydrocortisone aceponate, hydrocortisone, triamcinolone, methylprednisolone acetate, and the like. Suitable anti-fungal medicines include, without limitations chlotrimazole, econazole, itraconazole, ketoconazole, miconazole.

The compositions can contain, for example, from about 0.1% by weight, to about 90% or more by weight, of the antimicrobial peptide, depending on the method of administration. Where the compositions comprise dosage units, each unit can contain, for example, from about 0.5 mg to about 10 mg per dose of the antimicrobial peptide. For example, one dose of the composition may contain about 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg. The composition may contain about 1 to about 5 mg of the antimicrobial peptide per dose, or about 1.5 to about 5 mg of the antimicrobial peptide per dose, or about 2.5 mg to about 7.5 mg per dose, or about 1.5 mg to about 2.5 mg per dose, depending on the severity of the wound and the size of the animal.

Methods

In yet another aspect, the invention also provides methods of treating or preventing a bacterial infection in a subject, comprising administering an effective amount of one or more compounds described herein to the subject. Suitable subjects that can be treated include dogs, cats, horses, cattle, sheep, pigs, poultry, primates (e.g., rhesus monkeys and cynomolgus (also known as crab-eating or long-tailed) monkeys, marmosets, tamarinds, chimpanzees, macaques), rabbits, and rodents (rats, mice, guinea pigs and the like). In certain embodiment, the subject is a dog, and the antimicrobial peptide of the invention is delivered topically, intranasally, intraocularly, or intraaurally. The antimicrobial peptide may be delivered in a form of drops, spray, cream, gel, ointment and the like.

Infections that can be treated with the described compounds include external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, burns, antibacterial prophylaxis of surgery, and antibacterial prophylaxis in immunosuppressed subjects, such as patients receiving cancer chemotherapy, or organ transplant patients. These infections can be treated in hospital or community settings via various routes of administration as described herein.

The compounds or compositions described herein can also be used prophylactically. Accordingly, one or more of the present compounds or compositions can be administered to a subject deemed to be at risk for developing a microbial infection. Subjects at risk for developing a microbial infection include individuals who have been exposed to a particular microorganism, such as a pathogenic bacterial species; individuals having a compromised immune system, or subjects that are particularly vulnerable to the infections due to compromised natural defenses (e.g., where the skin is compromised due to burns or cuts).

The antimicrobial peptides described herein can be used for the treatment or prevention of infectious disorders caused by a variety of bacterial organisms, including infections by pathogenic bacterial species. Non-limiting examples of bacterial infection include Gram positive and Gram negative aerobic and anaerobic bacteria, such as Staphylococci, e.g., *S. aureus*; Enterococci, e.g., *E. faecalis*; Streptococci, e.g., *S. pyogenes* and *S. pneumoniae*; *Escherichia* species, e.g., *E. coli*, including enterotoxigenic, enteropathogenic, enteroinvasive, enterohemorrhagic and enteroaggregative *E. coli* strains; *Propionibacterium* strains, e.g., *P. acnes*; *Haemophilus*, e.g., *H. influenza*; *Moraxella*, e.g., *M. catarrhalis*. Other examples include Mycobacteria, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum*; Corynebacteria, e.g., *C. diphtheriae*; *Pseudomonas* species, e.g., *P. aeruginosa*; *Borrelia* species, e.g., *B. burgdorferi*; *Listeria* species, e.g., *L. monocytogenes*; *Bacillus* species, e.g., *B. cereus*; *Bordetella* species, e.g., *B. bronchiseptica*; *Klebsiella* species, *Clostridium* species, e.g., *C. perfringens, C. tetani*; *Chlamydia* species, e.g., *C. psittaci*; *Rickettsia* species, e.g., *R. rickettsii* and *R. prowazekii*; *Salmonella* species, e.g., *S. typhimurium*; *Yersinia* species, e.g., *Y. enterocolitica* and *Y. pseudotuberculosis*; *Klebsiella* species, e.g., *K. pneumoniae*; and *Mycoplasma*, e.g., *M. pneumonia, Actinobacillus* species, *H. parasuis*; and *Trueperella pyogenes*.

In certain aspects the bacteria are selected from Staphylococci, e.g., *S. pseudintermedius, S. aureus, S. schleiferi, S. chromogenes, S. simulans*, S. xylosus. The bacteria may also be selected from Streptococci, e.g., *S. uberis, S. agalactiae, S. dysgalactiae, S. suis*. Further, the bacteria of family Pasteurellaceae are suitable for treatment with the compositions described herein. Suitable Pasteurellaceae bacteria include *M. haemolytica, P. multocida, H. somni, Escherichia* species, e.g., *E. coli*, and *Klebsiella* species.

In certain embodiments, the bacteria are *S. pseudintermedius* and/or *P. aeruginosa*.

The compositions described herein may be administered in different frequency regiments. For example, suitable regimens include 4 times daily to once every week, e.g., three times daily, twice daily, once daily, every two days, every three days, twice per week, every five days and so on. Similarly, the inventions described herein may be administered in different duration regimens, e.g., in a single administration, for two days, for three days, for four days, for a week, for two weeks, for a month, for six weeks, and so on. The duration, the frequency and the amount of the antimicrobial peptide per dose, as well as the species and the state of the wound and/or state of the infection, may be considered together in determining the proper dose-time-frequency regimen for administration of the antimicrobial compositions claimed herein.

The following examples are presented as illustrative embodiments, but should not be taken as limiting the scope of the invention. Many changes, variations, modifications, and other uses and applications of this invention will be apparent to those skilled in the art.

EXAMPLES

Example 1. Antimicrobial Activity and Safety In Vitro

Peptides according to SEQ ID NOs as listed in Table 1 were prepared by a commercial manufacturer (CS Bio, Menlo Park, California) using solid phase synthesis. Antimicrobial activity was assessed by determining the Minimal Inhibitory Concentration (MIC) against *S. aureus* and *E. coli*. Briefly, Microbroth MICs were performed using CLSI methodology (VET01-S2). For *S. aureus* and *E. coli* ATCC strains, TSA with 5% lysed horse blood agar was used for overnight culturing at 37° C. ambient air. A 0.5 mM stock for each peptide was made with cell culture water, 0.01% acetic acid and serially diluted and spotted (10 μL) in a 96-well plate for in assay dose titration concentration of 50 μM to 0.05 μM. 0.5 McFarland Standard of each strain was diluted 1:250 in Mueller-Hinton Broth (MHB). 90 μL of culture suspension was then added upon drug in the 96-well plate for overnight incubation for 18-20 hours. The MIC was determined visually at the first well of no visible growth at the corresponding concentration.

The results of these experiments are provided in Table 1.

TABLE 1

| SEQ | Structure | S.aureus ATCC 29213 μM | E.coli ATCC 25922 μM |
|---|---|---|---|
| SEQ ID NO: 23 | KFCVYVCYRGICYRRCK | 1.6 | 0.4 |
| SEQ ID NO: 24 | KWCFRVCYRGVCYRRCR | 1.6 | 0.4 |
| SEQ ID NO: 1 | KWCFRVCYRGICYRRCRD | 1.6 | 0.4 |
| SEQ ID NO: 13 | KWCFRVCYRGICYRRCR | 3.1 | 0.8 |
| SEQ ID NO: 91 | GFCWYVCYRGFCYRRCN | 3.1 | 0.8 |
| SEQ ID NO: 92 | RGGRLCYCRRRFCVCVGR | 3.1 | 3.1 |
| SEQ ID NO: 93 | RRWCFRVCYRGFCYRKCR | 3.1 | 1.6 |
| SEQ ID NO: 28 | KWCFRVCYRGICYRKCR | 3.1 | 1.6 |
| SEQ ID NO: 94 | GFCWYVCRRRFCYRRCN | 3.1 | 0.4 |
| SEQ ID NO: 25 | KWCFRVCRRRFCYRRCR | 3.1 | 0.8 |
| SEQ ID NO: 26 | GFCWYVCYRGICYRRCN-NH2 | 3.1 | 0.8 |
| SEQ ID NO: 27 | GFCWYVCYRGFCYRRCN-NH2 | 3.1 | 0.8 |
| SEQ ID NO: 95 | GFCWYVCRRRFCYRRCN | 6.2 | 0.4 |
| SEQ ID NO: 33 | PGFCWYVCRRRFCYRRCN | 6.2 | 0.4 |
| SEQ ID NO: 34 | PFCWYVCRRRFCYRRCN | 6.2 | 0.4 |
| SEQ ID NO: 35 | GFCWYVCRRRFCHRRCN | 6.2 | 0.4 |
| SEQ ID NO: 36 | GVCVYVCRRRFCYRRCN | 6.2 | 0.4 |
| SEQ ID NO: 37 | GVCVYVCRRRFCYRRCN | 6.2 | 0.4 |
| SEQ ID NO: 38 | GFCWYVCRRRFCYRRCN-NH2 | 6.2 | 0.4 |
| SEQ ID NO: 39 | PGFCWYVCRRRFCYRRCND | 6.2 | 0.4 |

TABLE 1-continued

| SEQ | Structure | S.aureus ATCC 29213 µM | E.coli ATCC 25922 µM |
|---|---|---|---|
| SEQ ID NO: 40 | GFCWYVCRRRHCYRRCN | 6.2 | 0.8 |
| SEQ ID NO: 41 | KFCVYVCRRRFCYRRCK | 6.2 | 0.8 |
| SEQ ID NO: 42 | GHCWYVCRRRFCYRRCN | 6.2 | 0.4 |
| SEQ ID NO: 43 | GFCWYVCRRRFCYRRCS | 6.2 | 0.4 |
| SEQ ID NO: 44 | *GFCWYVCYRGICYRRCN-NH2 | 6.2 | 0.4 |
| SEQ ID NO: 45 | *GFCWYVCYRGFCYRRCN-NH2 | 6.2 | 0.8 |
| SEQ ID NO: 16 | GFCWYVCYRGICYRRCN | 6.25 | 0.4 |
| SEQ ID NO: 46 | GFCWYVCYRGFCYRRCN | 6.25 | 0.4 |
| SEQ ID NO: 47 | KFCWRVCRRRFCRRRCN | 12.5 | 0.8 |
| SEQ ID NO: 48 | GFCWYVCRRGFCYRRCN | 12.5 | 0.4 |
| SEQ ID NO: 49 | KWCFRVCRNGVCYRRCR | 12.5 | 0.2 |
| SEQ ID NO: 50 | GFCWYTCRRRFCYRRCN | 12.5 | 0.4 |
| SEQ ID NO: 51 | GFCWYVCYRGFCHRRCN | 25 | 6.2 |
| SEQ ID NO: 52 | GFCWYVCRRRFCHRRCN | 25 | 0.8 |
| SEQ ID NO: 53 | **GFCWYVCRRRFCYRRCN | 25 | 50 |
| SEQ ID NO: 54 | KFCWNVCRRRFCHRRCK | 25 | 0.4 |
| SEQ ID NO: 55 | GFCWYVCRRGICYRRCN | 25 | 0.8 |
| SEQ ID NO: 56 | GFCWYVCRRGICYRRCN | 25 | 0.8 |
| SEQ ID NO: 57 | GFCWNVCRRRFCRRRCN | 25 | 0.4 |
| SEQ ID NO: 58 | KFCVNVCYRGICHRRCK | 25 | 0.2 |
| SEQ ID NO: 59 | KFCVNVCRRRFCHRRCK | 25 | 0.8 |
| SEQ ID NO: 60 | KFCVNVCRRRFCRRRCK | 25 | 0.4 |
| SEQ ID NO: 61 | GFCWYVCYRGFCYQQCN | 25 | 6.2 |
| SEQ ID NO: 62 | GFCWYVCYRGFCYDDCN | 25 | 50 |
| SEQ ID NO: 63 | GFCWYVCPKGYCYRRCN | 50 | 50 |
| SEQ ID NO: 64 | GFCWYVCKNGFCYRRCN | 50 | 3.1 |
| SEQ ID NO: 65 | RKGCKCKNGFCVCR-NH2 | 50 | 6.25 |
| SEQ ID NO: 66 | GFCWNVCRRRFCHRRCN | 50 | 3.1 |
| SEQ ID NO: 67 | GFCWNVCRRRFCHRRCN | 50 | 1.6 |
| SEQ ID NO: 68 | GFCWNVCYRGICHRRCN | 50 | 1.6 |
| SEQ ID NO: 69 | KVCVNVCKQGICRKRCK | 50 | 50 |
| SEQ ID NO: 70 | GCWYVCRNGVCYRRCN | 50 | 25 |
| SEQ ID NO: 71 | GFCWYVCRNGVCYRRCN | 50 | 3.1 |
| SEQ ID NO: 72 | GFCWNVCYRGFCHRRCN | 50 | 3.1 |
| SEQ ID NO: 73 | GFCWYVCYRGFCYHHCN | 50 | 3.1 |
| SEQ ID NO: 74 | NVCVVRCRRGFCNRRCK | 50 | 12.5 |
| SEQ ID NO: 75 | KCVRVCRRRACRRRCK | 50 | 50 |
| SEQ ID NO: 76 | KCVRVCRRGFCNRRCK | 50 | 50 |

TABLE 1-continued

| SEQ | Structure | S.aureus ATCC 29213 μM | E.coli ATCC 25922 μM |
|---|---|---|---|
| SEQ ID NO: 77 | GFCWYVCKNGYCYRRCN | 50 | 3.1 |
| SEQ ID NO: 78 | GFCWYVCRNGYCYRRCN | 50 | 3.1 |
| SEQ ID NO: 79 | GFCWYVCRNGYCHRRCN | 50 | 6.2 |
| SEQ ID NO: 80 | GFCWYVCYRGICHRRCN | 50 | 1.6 |
| SEQ ID NO: 81 | KCVRVCRRGFCNRRCK | 50 | 50 |
| SEQ ID NO: 82 | GFCRYVCYRGICRRRCN | 50 | 6.2 |
| SEQ ID NO: 83 | KFCVNVCRNGICRRRCK | 50 | 1.6 |
| SEQ ID NO: 84 | GVCVNVCRRRFCHRRCN | 50 | 3.1 |
| SEQ ID NO: 85 | KKVCVNVCKQGICHKRCK | 50 | 50 |
| SEQ ID NO: 86 | KKVCVNVCRQGICHRRCK | 50 | 50 |
| SEQ ID NO: 87 | GFCRYVCRRGICRRRCN | 50 | 12.5 |
| SEQ ID NO: 88 | KFCVNVCYRGICRRRCK | 50 | 0.4 |
| SEQ ID NO: 89 | KCRRVCRRGFCYVVCN | 50 | 25 |
| SEQ ID NO: 90 | GHCHHVCRRRHCHRRCN | 50 | 50 |

*refers to N-acetylation
**refers to N-palmitic acid modification

SEQ ID NO: 1 was selected for further research. Toxicity of SEQ ID NO: 1 to eukaryotic blood cells was compared to that of tachyplesin (SEQ ID NO: 13). A standard, well referenced red blood cell hemolysis assay was employed against multiple species to test the lysis potential of the peptides. Red blood cells (RBCs) were prepared and isolated by several centrifuge and wash steps to remove the plasma fraction. A dose titration (50 μM to 0.05 μM) of test peptides and control peptide melittin were spotted from 50 mM stocks in a 384 well plate. Prepared RBCs were incubated with peptide for one hour at 37° C. Percent hemolysis was measured by optical density at 405 nm and utilizing 1% TritonX100 as hundred percent effect (HPE) and phosphate buffer alone as zero percent effect (ZPE).

The inventors have surprisingly discovered that SEQ ID NO: 1 had not only improved anti-microbial activity but also decreased toxicity to red blood cells. The results of the experiments using human, beagle, and rat red blood cells are illustrated in FIG. 1. Briefly, SEQ ID NO: 1 was 2-4 times less toxic to human, beagle or rat red blood cells than SEQ ID NO: 13. In mouse or bovine red blood cells, the differences were negligible.

Additional derivatives of SEQ ID NO: 1 have been synthesized by solid-phase synthesis as described above. Antimicrobial activity was assessed by determining MICs against S. aureus and E. coli, as described above. The results of these experiments are provided in Table 2.

TABLE 2

| SEQ ID | Sequence | S.aureus ATCC 29213 μM | E.coli 2 ATCC 5922 μM |
|---|---|---|---|
| SEQ ID NO: 3 | GWCFRVCYRGICYRRCRD | 6.2 | 3.1 |
| SEQ ID NO: 4 | KFCFRVCYRGICYRRCRD | 3.1 | 1.6 |
| SEQ ID NO: 5 | KWCFYVCYRGICYRRCRD | 6.2 | 1.6 |
| SEQ ID NO: 2 | RWCFRVCYRGICYRRCRD | 12.5 | 0.8 |
| SEQ ID NO: 6 | KWCFRVCRRGICYRRCRD | 12.5 | 3.1 |
| SEQ ID NO: 96 | KWCFRVCYGRICYRRCRD | 3.1 | 1.6 |
| SEQ ID NO: 7 | KWCFRVCYRGVCYRRCRD | 6.2 | 1.6 |
| SEQ ID NO: 8 | KWCFRVCYRGACYRRCRD | 3.1 | 1.6 |
| SEQ ID NO: 9 | KWCFRVCYRGFCYRRCRD | 6.2 | 3.1 |
| SEQ ID NO: 10 | KWCFRVCYRGICYHRCRD | 6.2 | 1.6 |

TABLE 2-continued

| SEQ ID | Sequence | S.aureus ATCC 29213 µM | E.coli 2 ATCC 5922 µM |
|---|---|---|---|
| SEQ ID NO: 11 | KWCFRVCYRGICYRRCND | 6.2 | 0.8 |
| SEQ ID NO: 1 | KWCFRVCYRGICYRRCRD | 3.1 | 0.8 |

Antimicrobial activity of the peptides listed in Table 2 against different strains of MSSP (Methicillin-Susceptible *Staphylococcus pseudintermedius*) and MRSP (Methicillin-Resistant *Staphylococcus pseudintermedius*) was further assessed. The results are in Tables 3 and 4, respectively.

TABLE 3

MIC against selected strains of MSSP

| SEQ ID | 49051 | 71990 | 72036 | 72191 | 76986 | 77378 | 78032 | 81923 | 84250 | 84658 | 86000 | 86001 |
|---|---|---|---|---|---|---|---|---|---|---|---|---|
| 3 | 1.6 | 1.6 | 1.6 | 1.6 | 1.6 | 0.4 | 1.6 | 1.6 | 1.6 | 1.6 | 1.6 | 0.8 |
| 4 | 1.6 | 1.6 | 0.8 | 0.8 | 0.8 | 0.4 | 0.8 | 1.6 | 1.6 | 1.6 | 1.6 | 0.8 |
| 5 | 1.6 | 1.6 | 1.6 | 1.6 | 1.6 | 0.8 | 1.6 | 1.6 | 1.6 | 1.6 | 1.6 | 1.6 |
| 2 | 1.6 | 1.6 | 1.6 | 1.6 | 1.6 | 1.6 | 1.6 | 3.1 | 1.6 | 3.1 | 1.6 | 1.6 |
| 6 | 3.1 | 3.1 | 3.1 | 3.1 | 3.1 | 1.6 | 3.1 | 3.1 | 3.1 | 3.1 | 3.1 | 3.1 |
| 96 | 1.6 | 1.6 | 1.6 | 1.6 | 1.6 | 0.8 | 1.6 | 1.6 | 1.6 | 1.6 | 1.6 | 1.6 |
| 7 | 1.6 | 1.6 | 1.6 | 1.6 | 1.6 | 0.8 | 1.6 | 1.6 | 1.6 | 1.6 | 1.6 | 1.6 |
| 8 | 1.6 | 1.6 | 1.6 | 1.6 | 1.6 | 0.8 | 1.6 | 3.1 | 1.6 | 1.6 | 1.6 | 1.6 |
| 9 | 1.6 | 1.6 | 0.8 | 1.6 | 0.8 | 0.4 | 0.8 | 1.6 | 1.6 | 1.6 | 0.8 | 0.8 |
| 10 | 1.6 | 1.6 | 1.6 | 1.6 | 1.6 | 0.8 | 1.6 | 1.6 | 1.6 | 1.6 | 1.6 | 1.6 |
| 11 | 0.8 | 1.6 | 0.8 | 0.8 | 0.8 | 0.4 | 0.8 | 1.6 | 0.8 | 0.8 | 0.4 | 0.8 |
| 1 | 1.6 | 1.6 | 1.6 | 1.6 | 1.6 | 1.6 | 1.6 | 1.6 | 1.6 | 1.6 | 1.6 | 1.6 |

TABLE 4

MIC against selected strains of MRSP

| SEQ ID | 71994 | 72035 | 72192 | 76923 | 79882 | 80729 | 81926 | 86002 | 87655 | 88493 |
|---|---|---|---|---|---|---|---|---|---|---|
| 3 | 1.6 | 1.6 | 1.6 | 1.6 | 0.8 | 1.6 | 1.6 | 1.6 | 1.6 | 1.6 |
| 4 | 1.6 | 1.6 | 1.6 | 0.8 | 0.8 | 0.8 | 0.8 | 1.6 | 1.6 | 1.6 |
| 5 | 1.6 | 1.6 | 1.6 | 1.6 | 1.6 | 1.6 | 1.6 | 1.6 | 1.6 | 1.6 |
| 2 | 1.6 | 1.6 | 1.6 | 1.6 | 0.8 | 1.6 | 1.6 | 1.6 | 1.6 | 1.6 |
| 6 | 3.1 | 3.1 | 3.1 | 3.1 | 3.1 | 3.1 | 3.1 | 3.1 | 3.1 | 3.1 |
| 96 | 1.6 | 1.6 | 1.6 | 1.6 | 1.6 | 1.6 | 1.6 | 1.6 | 1.6 | 1.6 |
| 7 | 1.6 | 1.6 | 1.6 | 1.6 | 1.6 | 1.6 | 1.6 | 1.6 | 1.6 | 1.6 |
| 8 | 1.6 | 1.6 | 1.6 | 1.6 | 1.6 | 1.6 | 1.6 | 1.6 | 1.6 | 1.6 |
| 9 | 1.6 | 1.6 | 1.6 | 1.6 | 0.8 | 1.6 | 1.6 | 1.6 | 1.6 | 1.6 |
| 10 | 1.6 | 1.6 | 1.6 | 1.6 | 0.8 | 1.6 | 1.6 | 1.6 | 1.6 | 1.6 |
| 11 | 1.6 | 1.6 | 0.8 | 0.8 | 0.8 | 0.8 | 0.8 | 0.8 | 0.8 | 1.6 |
| 1 | 1.6 | 1.6 | 1.6 | 1.6 | 1.6 | 1.6 | 1.6 | 1.6 | 1.6 | 1.6 |

Additional peptides were synthesized as described above. Antimicrobial properties of these peptides have been determined and are summarized below.

TABLE 5

Effect of selected antimicrobial sequences on strains of MSSP

| SEQ ID | 71990 | 72036 | 72191 | 76986 | 77378 | 78032 | 81923 | 84250 | 84658 | 86000 | 86001 |
|---|---|---|---|---|---|---|---|---|---|---|---|
| 97 | 3.1 | 3.1 | 3.1 | 1.6 | 1.6 | 3.1 | 3.1 | 3.1 | 3.1 | 1.6 | 1.6 |
| 98 | 1.6 | 1.6 | 1.6 | 1.6 | 1.6 | 1.6 | 1.6 | 1.6 | 1.6 | 1.6 | 1.6 |
| 99 | 1.6 | 1.6 | 3.1 | 1.6 | 1.6 | 1.6 | 1.6 | 3.1 | 3.1 | 3.1 | 1.6 |
| 100 | 1.6 | 1.6 | 3.1 | 1.6 | 3.1 | 1.6 | 1.6 | 1.6 | 1.6 | 1.6 | 1.6 |
| 102 | 1.6 | 1.6 | 3.1 | 1.6 | 0.8 | 1.6 | 1.6 | 1.6 | 1.6 | 1.6 | 1.6 |
| 103 | 3.1 | 3.1 | 3.1 | 3.1 | 3.1 | 3.1 | 3.1 | 6.2 | 3.1 | 3.1 | 3.1 |
| 104 | 1.6 | 3.1 | 1.6 | 1.6 | 1.6 | 1.6 | 3.1 | 3.1 | 1.6 | 3.1 | 1.6 |
| 105 | 1.6 | 1.6 | 1.6 | 1.6 | 0.8 | 1.6 | 1.6 | 1.6 | 3.1 | 1.6 | 1.6 |

TABLE 5-continued

Effect of selected antimicrobial sequences on strains of MSSP

| SEQ ID | 71990 | 72036 | 72191 | 76986 | 77378 | 78032 | 81923 | 84250 | 84658 | 86000 | 86001 |
|---|---|---|---|---|---|---|---|---|---|---|---|
| 106 | 1.6 | 1.6 | 1.6 | 1.6 | 0.8 | 1.6 | 1.6 | 1.6 | 1.6 | 1.6 | 1.6 |
| 107 | 1.6 | 1.6 | 1.6 | 1.6 | 1.6 | 1.6 | 1.6 | 1.6 | 1.6 | 1.6 | 1.6 |
| 108 | 3.1 | 3.1 | 3.1 | 3.1 | 3.1 | 3.1 | 3.1 | 3.1 | 3.1 | 3.1 | 3.1 |
| 109 | 1.6 | 1.6 | 1.6 | 1.6 | 1.6 | 1.6 | 1.6 | 1.6 | 1.6 | 1.6 | 1.6 |
| 110 | 1.6 | 3.1 | 3.1 | 1.6 | 1.6 | 1.6 | 3.1 | 3.1 | 3.1 | 3.1 | 3.1 |
| 112 | 1.6 | 1.6 | 1.6 | 1.6 | 0.8 | 1.6 | 1.6 | 1.6 | 1.6 | 1.6 | 1.6 |
| 113 | 1.6 | 1.6 | 1.6 | 1.6 | 1.6 | 1.6 | 1.6 | 1.6 | 1.6 | 1.6 | 1.6 |
| 114 | 1.6 | 3.1 | 3.1 | 1.6 | 1.6 | 3.1 | 3.1 | 3.1 | 3.1 | 3.1 | 1.6 |
| 115 | 1.6 | 1.6 | 1.6 | 1.6 | 0.8 | 1.6 | 1.6 | 1.6 | 1.6 | 1.6 | 1.6 |
| 116 | 1.6 | 1.6 | 1.6 | 1.6 | 1.6 | 1.6 | 1.6 | 1.6 | 1.6 | 1.6 | 1.6 |
| 117 | 1.6 | 1.6 | 1.6 | 0.8 | 0.8 | 1.6 | 1.6 | 1.6 | 1.6 | 1.6 | 1.6 |
| 32 | 1.6 | 1.6 | 1.6 | 1.6 | 1.6 | 1.6 | 1.6 | 3.1 | 3.1 | 1.6 | 1.6 |
| 28 | 1.6 | 1.6 | 1.6 | 0.8 | 1.6 | 1.6 | 1.6 | 1.6 | 1.6 | 1.6 | 1.6 |
| 29 | 1.6 | 1.6 | 1.6 | 1.6 | 0.8 | 0.8 | 0.8 | 0.8 | 1.6 | 1.6 | 1.6 |
| 30 | 0.8 | 0.8 | 1.6 | 0.8 | 0.8 | 0.8 | 0.8 | 0.8 | 1.6 | 1.6 | 1.6 |
| 31 | 1.6 | 1.6 | 1.6 | 1.6 | 1.6 | 1.6 | 1.6 | 1.6 | 1.6 | 1.6 | 1.6 |

TABLE 6

Effect of Antimicrobial peptides on different bacteria.

| SEQ ID | MR 71994 | MR 72035 | MR 72192 | MR 76923 | MR 79882 | MR 80279 | MR 81926 | MR 86002 | MR 87665 | Mr 88493 | SA 29213 | EC 25922 | SP 49051 |
|---|---|---|---|---|---|---|---|---|---|---|---|---|---|
| 97 | 1.6 | 3.1 | 3.1 | 1.6 | 1.6 | 3.1 | 1.6 | 3.1 | 3.1 | 3.1 | 6.2 | 3.1 | 3.1 |
| 98 | 1.6 | 3.1 | 1.6 | 1.6 | 0.8 | 1.6 | 1.6 | 1.6 | 1.6 | 1.6 | 3.1 | 1.6 | 1.6 |
| 99 | 1.6 | 3.1 | 3.1 | 1.6 | 1.6 | 1.6 | 3.1 | 3.1 | 1.6 | 1.6 | 6.2 | 1.6 | 3.1 |
| 100 | 1.6 | 3.1 | 1.6 | 1.6 | 1.6 | 1.6 | 1.6 | 1.6 | 1.6 | 3.1 | 6.2 | 0.8 | 1.6 |
| 102 | 3.1 | 3.1 | 1.6 | 1.6 | 1.6 | 1.6 | 1.6 | 1.6 | 1.6 | 3.1 | 6.2 | 1.6 | 1.6 |
| 103 | 3.1 | 3.1 | 3.1 | 3.1 | 3.1 | 3.1 | 3.1 | 3.1 | 3.1 | 3.1 | 25 | 6.2 | 3.1 |
| 104 | 3.1 | 1.6 | 1.6 | 1.6 | 1.6 | 1.6 | 1.6 | 1.6 | 3.1 | 3.1 | 6.2 | 3.1 | 1.6 |
| 105 | 1.6 | 1.6 | 1.6 | 1.6 | 0.8 | 1.6 | 1.6 | 1.6 | 1.6 | 3.1 | 6.2 | 1.6 | 1.6 |
| 106 | 1.6 | 3.1 | 1.6 | 1.6 | 0.8 | 1.6 | 1.6 | 1.6 | 1.6 | 3.1 | 3.1 | 3.1 | 1.6 |
| 107 | 1.6 | 3.1 | 1.6 | 1.6 | 0.8 | 1.6 | 1.6 | 1.6 | 1.6 | 1.6 | 3.1 | 3.1 | 1.6 |
| 108 | 3.1 | 3.1 | 3.1 | 3.1 | 3.1 | 3.1 | 3.1 | 3.1 | 3.1 | 3.1 | 12.5 | 0.8 | 3.1 |
| 109 | 1.6 | 1.6 | 1.6 | 1.6 | 0.8 | 1.6 | 1.6 | 1.6 | 1.6 | 1.6 | 3.1 | 1.6 | 1.6 |
| 110 | 3.1 | 3.1 | 3.1 | 3.1 | 1.6 | 1.6 | 3.1 | 3.1 | 3.1 | 3.1 | 6.2 | 1.6 | 3.1 |
| 112 | 1.6 | 1.6 | 1.6 | 1.6 | 0.8 | 0.8 | 1.6 | 1.6 | 1.6 | 1.6 | 3.1 | 1.6 | 1.6 |
| 113 | 1.6 | 1.6 | 1.6 | 1.6 | 1.6 | 1.6 | 1.6 | 1.6 | 1.6 | 1.6 | 6.2 | 1.6 | 1.6 |
| 114 | 3.1 | 3.1 | 3.1 | 3.1 | 1.6 | 1.6 | 3.1 | 3.1 | 3.1 | 3.1 | 6.2 | 1.6 | 3.1 |
| 115 | 1.6 | 1.6 | 1.6 | 1.6 | 0.8 | 1.6 | 1.6 | 1.6 | 1.6 | 1.6 | 3.1 | 0.8 | 1.6 |
| 116 | 1.6 | 1.6 | 1.6 | 1.6 | 1.6 | 1.6 | 3.1 | 1.6 | 1.6 | 1.6 | 6.2 | 0.8 | 1.6 |
| 117 | 1.6 | 1.6 | 0.8 | 1.6 | 0.8 | 1.6 | 1.6 | 0.8 | 1.6 | 1.6 | 6.2 | 0.8 | 1.6 |
| 32 | 3.1 | 3.1 | 1.6 | 3.1 | 1.6 | 1.6 | 3.1 | 1.6 | 1.6 | 1.6 | 12.5 | 1.6 | 3.1 |
| 28 | 1.6 | 3.1 | 3.1 | 1.6 | 0.8 | 1.6 | 1.6 | 1.6 | 1.6 | 1.6 | 6.2 | 0.8 | 1.6 |
| 29 | 1.6 | 1.6 | 0.8 | 1.6 | 0.8 | 0.8 | 0.8 | 1.6 | 1.6 | 1.6 | 3.1 | 1.6 | 1.6 |
| 30 | 1.6 | 0.8 | 0.8 | 0.8 | 0.8 | 0.8 | 1.6 | 1.6 | 1.6 | 1.6 | 3.1 | 1.6 | 1.6 |
| 31 | 1.6 | 1.6 | 1.6 | 1.6 | 1.6 | 1.6 | 1.6 | 1.6 | 1.6 | 1.6 | 3.1 | 1.6 | 1.6 |

MR = MRSP,
SA = S. aureus,
EC = E. coli
SP = S. pseudintermedius

Safety of the peptides listed in table 2 was determining by measuring cell viability. Canine-derived epithelial keratinocyte (CPEK) cells were propagated to determine cell viability in the presence of peptides. Cells were grown from a frozen stock in CnT-09-5 (with supplements) pre-warmed media in a T75 flask and incubated overnight at 37° C., 5% $CO_2$. Cells were washed with phosphate buffer and replenished with pre-warmed CnT-05-9 media and repeated for several days until cells reached a density of $6.6 \times 10^4$ cells/mL. Cells were then transferred to a 384 well plate, allowed to settle and dosed with peptides and melittin control peptide (50 μM to 0.05 μM) and incubated overnight at 37° C., 5% $CO_2$. 0.1% TritonX100 as (HPE) and phosphate buffer alone as (ZPE) were added to the plates to calculate percent effect once the assay was terminated with 10 μL CELLTITER-GLO® assay reagents for a luminescent readout. The results are provided in Table 7.

TABLE 7

| SEQ ID NO: | CPEK (50 μM) | cRBC (50 μM) |
|---|---|---|
| 3 | 42.1 | 67.1 |
| 4 | 16.6 | 67.1 |
| 5 | 28.6 | 3.1 |
| 2 | -1.7 | 64.0 |
| 6 | 4.1 | 1.1 |
| 96 | 51.9 | 101.4 |
| 7 | 11.3 | 84.1 |

TABLE 7-continued

| SEQ ID NO: | CPEK (50 μM) | cRBC (50 μM) |
|---|---|---|
| 8 | 24.6 | 30.2 |
| 9 | 52.3 | 101.3 |
| 10 | 31.5 | 101.1 |
| 11 | 22.0 | 57.8 |
| 1 | 21.5 | 20.5 |

Safety of the peptides listed in table 6 was determining by measuring cell viability as described above. The results are provided in Table 8.

TABLE 8

| SEQ ID | cRBC (50 μM) | CPEK (50 μM) |
|---|---|---|
| 97 | 31.2 | 12.9 |
| 98 | 35.0 | 9.3 |
| 99 | 100.0 | 19.9 |
| 100 | 100.0 | 29.5 |
| 102 | 23.9 | -2.1 |
| 103 | 7.9 | -0.5 |
| 104 | 100.6 | 6.0 |
| 105 | 97.9 | 8.6 |
| 106 | 101.5 | 25.2 |
| 107 | 101.8 | 26.3 |
| 108 | 27.7 | 9.6 |
| 109 | 99.8 | 19.2 |
| 110 | 46.3 | 10.7 |
| 112 | 61.0 | 14.2 |
| 113 | 86.3 | 15.7 |
| 114 | 97.9 | 11.9 |

TABLE 8-continued

| SEQ ID | cRBC (50 μM) | CPEK (50 μM) |
|---|---|---|
| 115 | 94.6 | 5.1 |
| 116 | 87.0 | 16.0 |
| 117 | 97.8 | 14.7 |
| 32 | 98.3 | 9.1 |
| 28 | 94.4 | 19.4 |
| 29 | 68.2 | 17.5 |
| 30 | 63.5 | 17.0 |
| 31 | 43.5 | 11.0 |

These data demonstrate that the antimicrobial peptides of the instant invention are not only effective against the tested strains of bacteria but also safe, particularly for non-systemic, e.g., topical, administration.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method of treating an ear infection in an animal in need thereof, the method comprising administering to said animal a formulation comprising an amino acid sequence that is 18-21 amino acids long and comprises, at the N-terminus, SEQ ID NO: 1 (KWCFRVCYRGICYRRCRD) or SEQ ID NO: 29 (PKWCFRVCYRGICYRRCRD) or a peptide that differs from SEQ ID NO: 1 or SEQ ID NO: 29 by one, two, three, or four amino acids, wherein the amino acids differing from the amino acids of SEQ ID NO: 1 or SEQ ID NO: 29 are independently selected from the group consisting of arginine or glycine at the position corresponding to position 1 of SEQ ID NO: 1;
phenylalanine or arginine at the position corresponding to position 2 of SEQ ID NO: 1;
valine or tryptophan at the position corresponding to position 4 of SEQ ID NO: 1;
tyrosine at the position corresponding to position 5 of SEQ ID NO: 1;
arginine at the position corresponding to position 8 of SEQ ID NO: 1;
glycine at the position corresponding to position 9 of SEQ ID NO: 1;
arginine at the position corresponding to position 10 of SEQ ID NO: 1;
alanine, phenylalanine, or valine at the position corresponding to position 11 of SEQ ID NO: 1;
histidine at the position corresponding to position 14 of SEQ ID NO: 1;
lysine at the position corresponding to position 15 of SEQ ID NO: 1; and
asparagine at the position corresponding to position 17 of SEQ ID NO: 1.

2. The method according to claim 1, wherein the amino acid sequence comprises asparagine at the position corresponding to position 17 of SEQ ID NO: 1.

3. The method according to claim 1, wherein the amino acid sequence comprises glycine at the position corresponding to position 1 of SEQ ID NO: 1.

4. The method according to claim 1, wherein the amino acid sequence comprises alanine at the position corresponding to position 11 of SEQ ID NO: 1.

5. The method according to claim 1, wherein, in said amino acid sequence, arginine is present at the position corresponding to position 14 of SEQ ID NO: 1, at the position corresponding to position 15 of SEQ ID NO: 1, or both.

6. The method according to claim 1, wherein the amino acid sequence comprises arginine at the position corresponding to position 14 of SEQ ID NO: 1 and at the position corresponding to position 15 of SEQ ID NO: 1.

7. The method according to claim 1, wherein said amino acid sequence is 18 amino acids long.

8. The method of claim 1, wherein the peptide differs from SEQ ID NO: 1 by three, two, or one amino acid(s).

9. The method according to claim 1 wherein the amino acid sequence comprises, at the N-terminus, SEQ ID NO: 1, SEQ ID NO: 2 (RWCFRVCYRGICYRRCRD), SEQ ID NO: 3 (GWCFRVCYRGICYRRCRD), SEQ ID NO: 4 (KFCFRVCYRGICYRRCRD); SEQ ID NO: 5 (KWCFYVCYRGICYRRCRD), SEQ ID NO: 6 (KWCFRVCRRGICYRRCRD), SEQ ID NO: 7 (KWCFRVCYRGVCYRRCRD), SEQ ID NO: 8 (KWCFRVCYRGACYRRCRD), SEQ ID NO: 9 (KWCFRVCYRGFCYRRCRD), SEQ ID NO: 10 (KWCFRVCYRGICYHRCRD), SEQ ID NO: 11 (KWCFRVCYRGICYRRCND).

10. The method according to claim 9, wherein the amino acid sequence comprises SEQ ID NO: 1 or SEQ ID NO: 3.

11. The method according to claim 9, wherein the amino acid sequence comprises SEQ ID NO: 4, SEQ ID NO: 5, SEQ ID NO: 6, or SEQ ID NO: 8.

12. The method of claim 1, wherein the amino acid sequence is SEQ ID NO: 1 or the peptide differs therefrom by one amino acid.

13. The method according to claim 1, wherein said amino acid sequence is 19 amino acids long.

14. The method of claim 13, wherein the peptide differs from SEQ ID NO: 29 by three, two, or one amino acid(s).

15. The method of claim 14, wherein the amino acid sequence is SEQ ID NO: 29 or the peptide differs therefrom by one amino acid.

16. The method of claim 1, wherein said amino acid sequence consists of SEQ ID NO: 1 or SEQ ID NO: 29.

17. The method of claim 16, wherein said animal is a dog.

18. The method of claim 1, wherein said animal is a dog.

* * * * *

SEQUENCE LISTING

```
<160> NUMBER OF SEQ ID NOS: 117

<210> SEQ ID NO 1
<211> LENGTH: 18
<212> TYPE: PRT
<213> ORGANISM: Artificial Sequence
<220> FEATURE:
<223> OTHER INFORMATION: Antimicrobial peptide

<400> SEQUENCE: 1

Lys Trp Cys Phe Arg Val Cys Tyr Arg Gly Ile Cys Tyr Arg Arg Cys
1               5                   10                  15

Arg Asp

<210> SEQ ID NO 2
<211> LENGTH: 18
<212> TYPE: PRT
<213> ORGANISM: Artificial Sequence
<220> FEATURE:
<223> OTHER INFORMATION: Artificial antimicrobial peptide

<400> SEQUENCE: 2

Arg Trp Cys Phe Arg Val Cys Tyr Arg Gly Ile Cys Tyr Arg Arg Cys
1               5                   10                  15

Arg Asp

<210> SEQ ID NO 3
<211> LENGTH: 18
<212> TYPE: PRT
<213> ORGANISM: Artificial Sequence
<220> FEATURE:
```

<223> OTHER INFORMATION: Artificial Antimicrobial peptide

<400> SEQUENCE: 3

Gly Trp Cys Phe Arg Val Cys Tyr Arg Gly Ile Cys Tyr Arg Arg Cys
1               5                   10                  15

Arg Asp

<210> SEQ ID NO 4
<211> LENGTH: 18
<212> TYPE: PRT
<213> ORGANISM: Artificial Sequence
<220> FEATURE:
<223> OTHER INFORMATION: Artificial antimicrobial peptide

<400> SEQUENCE: 4

Lys Phe Cys Phe Arg Val Cys Tyr Arg Gly Ile Cys Tyr Arg Arg Cys
1               5                   10                  15

Arg Asp

<210> SEQ ID NO 5
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 5

Lys Trp Cys Phe Tyr Val Cys Tyr Arg Gly Ile Cys Tyr Arg Arg Cys
1               5                   10                  15

Arg Asp

<210> SEQ ID NO 6
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 6

Lys Trp Cys Phe Arg Val Cys Arg Arg Gly Ile Cys Tyr Arg Arg Cys
1               5                   10                  15

Arg Asp

<210> SEQ ID NO 7
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 7

Lys Trp Cys Phe Arg Val Cys Tyr Arg Gly Val Cys Tyr Arg Arg Cys
1               5                   10                  15

Arg Asp

<210> SEQ ID NO 8
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 8

```
Lys Trp Cys Phe Arg Val Cys Tyr Arg Gly Ala Cys Tyr Arg Arg Cys
1               5                   10                  15

Arg Asp

<210> SEQ ID NO 9
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 9

Lys Trp Cys Phe Arg Val Cys Tyr Arg Gly Phe Cys Tyr Arg Arg Cys
1               5                   10                  15

Arg Asp

<210> SEQ ID NO 10
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 10

Lys Trp Cys Phe Arg Val Cys Tyr Arg Gly Ile Cys Tyr His Arg Cys
1               5                   10                  15

Arg Asp

<210> SEQ ID NO 11
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 11

Lys Trp Cys Phe Arg Val Cys Tyr Arg Gly Ile Cys Tyr Arg Arg Cys
1               5                   10                  15

Asn Asp

<210> SEQ ID NO 12
<211> LENGTH: 19
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: misc_feature
<222> LOCATION: (1)..(1)
<223> OTHER INFORMATION: Absent or Proline
<220> FEATURE:
<221> NAME/KEY: misc_feature
<222> LOCATION: (2)..(2)
<223> OTHER INFORMATION: Lysine, Arginine, Glycine, or Proline
<220> FEATURE:
<221> NAME/KEY: misc_feature
<222> LOCATION: (3)..(3)
<223> OTHER INFORMATION: Phenylalanine, Tryptophan or Arginine
<220> FEATURE:
<221> NAME/KEY: misc_feature
<222> LOCATION: (5)..(5)
<223> OTHER INFORMATION: phenylalanine, valine or tryptophan
<220> FEATURE:
<221> NAME/KEY: misc_feature
<222> LOCATION: (6)..(6)
<223> OTHER INFORMATION: arginine, tyrosine or phenylalanine
<220> FEATURE:
<221> NAME/KEY: misc_feature
```

```
<222> LOCATION: (7)..(7)
<223> OTHER INFORMATION: valine or alanine
<220> FEATURE:
<221> NAME/KEY: misc_feature
<222> LOCATION: (9)..(9)
<223> OTHER INFORMATION: tyrosine, arginine, lysine or tryptophan
<220> FEATURE:
<221> NAME/KEY: misc_feature
<222> LOCATION: (10)..(10)
<223> OTHER INFORMATION: arginine, phenylalanine, or glycine
<220> FEATURE:
<221> NAME/KEY: misc_feature
<222> LOCATION: (11)..(11)
<223> OTHER INFORMATION: arginine or glycine
<220> FEATURE:
<221> NAME/KEY: misc_feature
<222> LOCATION: (12)..(12)
<223> OTHER INFORMATION: isoleucine, alanine, phenylalanine, tyrosine or
      valine
<220> FEATURE:
<221> NAME/KEY: misc_feature
<222> LOCATION: (15)..(15)
<223> OTHER INFORMATION: arginine or histidine
<220> FEATURE:
<221> NAME/KEY: misc_feature
<222> LOCATION: (16)..(16)
<223> OTHER INFORMATION: arginine or lysine
<220> FEATURE:
<221> NAME/KEY: misc_feature
<222> LOCATION: (18)..(18)
<223> OTHER INFORMATION: arginine, lysine, alanine, or asparagine
<220> FEATURE:
<221> NAME/KEY: misc_feature
<222> LOCATION: (19)..(19)
<223> OTHER INFORMATION: Any amino acid, may be 0-4 amino acids long

<400> SEQUENCE: 12

Xaa Xaa Xaa Cys Xaa Xaa Xaa Cys Xaa Xaa Xaa Xaa Cys Tyr Xaa Xaa
1               5                   10                  15

Cys Xaa Xaa

<210> SEQ ID NO 13
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 13

Lys Trp Cys Phe Arg Val Cys Tyr Arg Gly Ile Cys Tyr Arg Arg Cys
1               5                   10                  15

Arg

<210> SEQ ID NO 14
<211> LENGTH: 4
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: PEPTIDE
<222> LOCATION: (1)..(4)
<223> OTHER INFORMATION: Not Arg Arg Arg Phe

<400> SEQUENCE: 14

Xaa Xaa Xaa Xaa
1

<210> SEQ ID NO 15
<211> LENGTH: 4
<212> TYPE: PRT
```

```
<213> ORGANISM: Artificial Sequence
<220> FEATURE:
<223> OTHER INFORMATION: Artificial Antimicrobial peptide

<400> SEQUENCE: 15

Arg Arg Arg Phe
1

<210> SEQ ID NO 16
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 16

Gly Phe Cys Trp Tyr Val Cys Tyr Arg Gly Ile Cys Tyr Arg Arg Cys
1               5                  10                  15

Asn

<210> SEQ ID NO 17
<211> LENGTH: 4
<212> TYPE: PRT
<213> ORGANISM: Artificial Sequence
<220> FEATURE:
<223> OTHER INFORMATION: Artificial Antimicrobial peptide

<400> SEQUENCE: 17

Tyr Arg Gly Ile
1

<210> SEQ ID NO 18
<211> LENGTH: 4
<212> TYPE: PRT
<213> ORGANISM: Artificial Sequence
<220> FEATURE:
<223> OTHER INFORMATION: Artificial Antimicrobial peptide fragment

<400> SEQUENCE: 18

Tyr Arg Gly Val
1

<210> SEQ ID NO 19
<211> LENGTH: 4
<212> TYPE: PRT
<213> ORGANISM: Artificial Sequence
<220> FEATURE:
<223> OTHER INFORMATION: Artificial Antimicrobial peptide fragment

<400> SEQUENCE: 19

Tyr Arg Gly Phe
1

<210> SEQ ID NO 20
<211> LENGTH: 3
<212> TYPE: PRT
<213> ORGANISM: Artificial Sequence
<220> FEATURE:
<223> OTHER INFORMATION: Artificial Antimicrobial peptide fragment
<220> FEATURE:
<221> NAME/KEY: peptide
<222> LOCATION: (1)..(3)
<223> OTHER INFORMATION: Phe Arg Val or Trp Tyr Val

<400> SEQUENCE: 20

Xaa Xaa Xaa
1
```

```
<210> SEQ ID NO 21
<211> LENGTH: 3
<212> TYPE: PRT
<213> ORGANISM: Artificial Sequence
<220> FEATURE:
<223> OTHER INFORMATION: Artificial Antimicrobial peptide fragment

<400> SEQUENCE: 21

Phe Arg Val
1

<210> SEQ ID NO 22
<211> LENGTH: 3
<212> TYPE: PRT
<213> ORGANISM: Artificial Sequence
<220> FEATURE:
<223> OTHER INFORMATION: Artificial Antimicrobial peptide fragment

<400> SEQUENCE: 22

Trp Tyr Val
1

<210> SEQ ID NO 23
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 23

Lys Phe Cys Val Tyr Val Cys Tyr Arg Gly Ile Cys Tyr Arg Arg Cys
1               5                   10                  15

Lys

<210> SEQ ID NO 24
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 24

Lys Trp Cys Phe Arg Val Cys Tyr Arg Gly Val Cys Tyr Arg Arg Cys
1               5                   10                  15

Arg

<210> SEQ ID NO 25
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 25

Lys Trp Cys Phe Arg Val Cys Arg Arg Arg Phe Cys Tyr Arg Arg Cys
1               5                   10                  15

Arg

<210> SEQ ID NO 26
<211> LENGTH: 17
<212> TYPE: PRT
<213> ORGANISM: Artificial Sequence
<220> FEATURE:
<223> OTHER INFORMATION: Artificial Antimicrobial peptide
```

```
<220> FEATURE:
<221> NAME/KEY: Mod_res
<222> LOCATION: (17)..(17)
<223> OTHER INFORMATION: Amidated

<400> SEQUENCE: 26

Gly Phe Cys Trp Tyr Val Cys Tyr Arg Gly Ile Cys Tyr Arg Arg Cys
1               5                   10                  15
Asn

<210> SEQ ID NO 27
<211> LENGTH: 17
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: MOD_RES
<222> LOCATION: (17)..(17)
<223> OTHER INFORMATION: Amidated

<400> SEQUENCE: 27

Gly Phe Cys Trp Tyr Val Cys Tyr Arg Gly Phe Cys Tyr Arg Arg Cys
1               5                   10                  15
Asn

<210> SEQ ID NO 28
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 28

Pro Lys Trp Cys Phe Arg Val Cys Tyr Arg Gly Ile Cys Tyr Arg Arg
1               5                   10                  15
Cys Arg

<210> SEQ ID NO 29
<211> LENGTH: 19
<212> TYPE: PRT
<213> ORGANISM: Artificial Sequence
<220> FEATURE:
<223> OTHER INFORMATION: Artificial Antimicrobial peptide

<400> SEQUENCE: 29

Pro Lys Trp Cys Phe Arg Val Cys Tyr Arg Gly Ile Cys Tyr Arg Arg
1               5                   10                  15
Cys Arg Asp

<210> SEQ ID NO 30
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 30

Pro Trp Cys Phe Arg Val Cys Tyr Arg Gly Ile Cys Tyr Arg Arg Cys
1               5                   10                  15
Arg

<210> SEQ ID NO 31
<211> LENGTH: 18
```

```
<212> TYPE: PRT
<213> ORGANISM: Artificial Sequence
<220> FEATURE:
<223> OTHER INFORMATION: Artificial Antimicrobial peptide

<400> SEQUENCE: 31

Pro Trp Cys Phe Arg Val Cys Tyr Arg Gly Ile Cys Tyr Arg Arg Cys
1               5                   10                  15

Arg Asp

<210> SEQ ID NO 32

<400> SEQUENCE: 32

000

<210> SEQ ID NO 33
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 33

Pro Gly Phe Cys Trp Tyr Val Cys Arg Arg Arg Phe Cys Tyr Arg Arg
1               5                   10                  15

Cys Asn

<210> SEQ ID NO 34
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 34

Pro Phe Cys Trp Tyr Val Cys Arg Arg Arg Phe Cys Tyr Arg Arg Cys
1               5                   10                  15

Asn

<210> SEQ ID NO 35
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 35

Gly Phe Cys Trp Tyr Val Cys Arg Arg Arg Phe Cys His Arg Arg Cys
1               5                   10                  15

Asn

<210> SEQ ID NO 36
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 36

Gly Val Cys Val Tyr Val Cys Arg Arg Arg Phe Cys Tyr Arg Arg Cys
1               5                   10                  15

Asn
```

```
<210> SEQ ID NO 37
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 37

Gly Val Cys Val Tyr Val Cys Arg Arg Arg Phe Cys Tyr Arg Arg Cys
1               5                   10                  15

Asn

<210> SEQ ID NO 38
<211> LENGTH: 17
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: MOD_RES
<222> LOCATION: (17)..(17)
<223> OTHER INFORMATION: Amidation

<400> SEQUENCE: 38

Gly Phe Cys Trp Tyr Val Cys Arg Arg Arg Phe Cys Tyr Arg Arg Cys
1               5                   10                  15

Asn

<210> SEQ ID NO 39
<211> LENGTH: 19
<212> TYPE: PRT
<213> ORGANISM: Artificial Sequence
<220> FEATURE:
<223> OTHER INFORMATION: Artificial Antimicrobial peptide

<400> SEQUENCE: 39

Pro Gly Phe Cys Trp Tyr Val Cys Arg Arg Arg Phe Cys Tyr Arg Arg
1               5                   10                  15

Cys Asn Asp

<210> SEQ ID NO 40
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 40

Gly Phe Cys Trp Tyr Val Cys Arg Arg Arg His Cys Tyr Arg Arg Cys
1               5                   10                  15

Asn

<210> SEQ ID NO 41
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 41

Lys Phe Cys Val Tyr Val Cys Arg Arg Arg Phe Cys Tyr Arg Arg Cys
1               5                   10                  15

Lys
```

```
<210> SEQ ID NO 42
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 42

Gly His Cys Trp Tyr Val Cys Arg Arg Arg Phe Cys Tyr Arg Arg Cys
1               5                   10                  15

Asn

<210> SEQ ID NO 43
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 43

Gly Phe Cys Trp Tyr Val Cys Arg Arg Arg Phe Cys Tyr Arg Arg Cys
1               5                   10                  15

Ser

<210> SEQ ID NO 44
<211> LENGTH: 17
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: MOD_RES
<222> LOCATION: (1)..(1)
<223> OTHER INFORMATION: N-Acetylated
<220> FEATURE:
<221> NAME/KEY: MOD_RES
<222> LOCATION: (17)..(17)
<223> OTHER INFORMATION: Amidated

<400> SEQUENCE: 44

Gly Phe Cys Trp Tyr Val Cys Tyr Arg Gly Ile Cys Tyr Arg Arg Cys
1               5                   10                  15

Asn

<210> SEQ ID NO 45
<211> LENGTH: 17
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: Mod-res
<222> LOCATION: (1)..(1)
<223> OTHER INFORMATION: N-Acetylated
<220> FEATURE:
<221> NAME/KEY: Mod-res
<222> LOCATION: (17)..(17)
<223> OTHER INFORMATION: Amidated

<400> SEQUENCE: 45

Gly Phe Cys Trp Tyr Val Cys Tyr Arg Gly Phe Cys Tyr Arg Arg Cys
1               5                   10                  15

Asn

<210> SEQ ID NO 46
<211> LENGTH: 17
```

<212> TYPE: PRT
<213> ORGANISM: Artificial Sequence
<220> FEATURE:
<223> OTHER INFORMATION: Artificial Antimicrobial peptide

<400> SEQUENCE: 46

Gly Phe Cys Trp Tyr Val Cys Tyr Arg Gly Phe Cys Tyr Arg Arg Cys
1               5                   10                  15

Asn

<210> SEQ ID NO 47
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 47

Lys Phe Cys Trp Arg Val Cys Arg Arg Arg Phe Cys Arg Arg Arg Cys
1               5                   10                  15

Asn

<210> SEQ ID NO 48
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 48

Gly Phe Cys Trp Tyr Val Cys Arg Arg Gly Phe Cys Tyr Arg Arg Cys
1               5                   10                  15

Asn

<210> SEQ ID NO 49
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 49

Lys Trp Cys Phe Arg Val Cys Arg Asn Gly Val Cys Tyr Arg Arg Cys
1               5                   10                  15

Arg

<210> SEQ ID NO 50
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 50

Gly Phe Cys Trp Tyr Thr Cys Arg Arg Arg Phe Cys Tyr Arg Arg Cys
1               5                   10                  15

Asn

<210> SEQ ID NO 51
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 51

Gly Phe Cys Trp Tyr Val Cys Tyr Arg Gly Phe Cys His Arg Arg Cys
1               5                   10                  15

Asn

<210> SEQ ID NO 52
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 52

Gly Phe Cys Trp Tyr Val Cys Arg Arg Arg Phe Cys His Arg Arg Cys
1               5                   10                  15

Asn

<210> SEQ ID NO 53
<211> LENGTH: 17
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: mod-res
<222> LOCATION: (1)..(1)
<223> OTHER INFORMATION: N-Palmitoylated

<400> SEQUENCE: 53

Gly Phe Cys Trp Tyr Val Cys Arg Arg Arg Phe Cys Tyr Arg Arg Cys
1               5                   10                  15

Asn

<210> SEQ ID NO 54
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 54

Lys Phe Cys Trp Asn Val Cys Arg Arg Arg Phe Cys His Arg Arg Cys
1               5                   10                  15

Lys

<210> SEQ ID NO 55
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 55

Gly Phe Cys Trp Tyr Val Cys Arg Arg Gly Ile Cys Tyr Arg Arg Cys
1               5                   10                  15

Asn

<210> SEQ ID NO 56
<211> LENGTH: 17
<212> TYPE: PRT
<213> ORGANISM: Artificial Sequence
<220> FEATURE:
<223> OTHER INFORMATION: Artificial Antimicrobial peptide -continued

```
<400> SEQUENCE: 56

Gly Phe Cys Trp Tyr Val Cys Arg Arg Gly Ile Cys Tyr Arg Arg Cys
1               5                   10                  15

Asn

<210> SEQ ID NO 57
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 57

Gly Phe Cys Trp Asn Val Cys Arg Arg Arg Phe Cys Arg Arg Arg Cys
1               5                   10                  15

Asn

<210> SEQ ID NO 58
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 58

Lys Phe Cys Val Asn Val Cys Tyr Arg Gly Ile Cys His Arg Arg Cys
1               5                   10                  15

Lys

<210> SEQ ID NO 59
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 59

Lys Phe Cys Val Asn Val Cys Arg Arg Arg Phe Cys His Arg Arg Cys
1               5                   10                  15

Lys

<210> SEQ ID NO 60
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 60

Lys Phe Cys Val Asn Val Cys Arg Arg Arg Phe Cys Arg Arg Arg Cys
1               5                   10                  15

Lys

<210> SEQ ID NO 61
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 61

Gly Phe Cys Trp Tyr Val Cys Tyr Arg Gly Phe Cys Tyr Gln Gln Cys
```

```
1               5                   10                  15

Asn

<210> SEQ ID NO 62
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 62

Gly Phe Cys Trp Tyr Val Cys Tyr Arg Gly Phe Cys Tyr Asp Asp Cys
1               5                   10                  15

Asn

<210> SEQ ID NO 63
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 63

Gly Phe Cys Trp Tyr Val Cys Pro Lys Gly Tyr Cys Tyr Arg Arg Cys
1               5                   10                  15

Asn

<210> SEQ ID NO 64
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 64

Gly Phe Cys Trp Tyr Val Cys Lys Asn Gly Phe Cys Tyr Arg Arg Cys
1               5                   10                  15

Asn

<210> SEQ ID NO 65
<211> LENGTH: 14
<212> TYPE: PRT
<213> ORGANISM: Artificial Sequence
<220> FEATURE:
<223> OTHER INFORMATION: Artificial Antimicrobial peptide
<220> FEATURE:
<221> NAME/KEY: mod_res
<222> LOCATION: (14)..(14)
<223> OTHER INFORMATION: Amidated

<400> SEQUENCE: 65

Arg Lys Gly Cys Lys Cys Lys Asn Gly Phe Cys Val Cys Arg
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 66

Gly Phe Cys Trp Asn Val Cys Arg Arg Phe Cys His Arg Arg Cys
1               5                   10                  15
```

-continued

Asn

<210> SEQ ID NO 67
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 67

Gly Phe Cys Trp Asn Val Cys Arg Arg Arg Phe Cys His Arg Arg Cys
1               5                   10                  15

Asn

<210> SEQ ID NO 68
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 68

Gly Phe Cys Trp Asn Val Cys Tyr Arg Gly Ile Cys His Arg Arg Cys
1               5                   10                  15

Asn

<210> SEQ ID NO 69
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 69

Lys Val Cys Val Asn Val Cys Lys Gln Gly Ile Cys Arg Lys Arg Cys
1               5                   10                  15

Lys

<210> SEQ ID NO 70
<211> LENGTH: 16
<212> TYPE: PRT
<213> ORGANISM: Artificial Sequence
<220> FEATURE:
<223> OTHER INFORMATION: Artificial Antimicrobial peptide

<400> SEQUENCE: 70

Gly Cys Trp Tyr Val Cys Arg Asn Gly Val Cys Tyr Arg Arg Cys Asn
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 71

Gly Phe Cys Trp Tyr Val Cys Arg Asn Gly Val Cys Tyr Arg Arg Cys
1               5                   10                  15

Asn

<210> SEQ ID NO 72
<211> LENGTH: 17
<212> TYPE: PRT

<213> ORGANISM: Artificial Sequence
<220> FEATURE:
<223> OTHER INFORMATION: Artificial Antimicrobial peptide

<400> SEQUENCE: 72

Gly Phe Cys Trp Asn Val Cys Tyr Arg Gly Phe Cys His Arg Cys
1               5                   10                  15

Asn

<210> SEQ ID NO 73
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 73

Gly Phe Cys Trp Tyr Val Cys Tyr Arg Gly Phe Cys Tyr His His Cys
1               5                   10                  15

Asn

<210> SEQ ID NO 74
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 74

Asn Val Cys Val Val Arg Cys Arg Arg Gly Phe Cys Asn Arg Arg Cys
1               5                   10                  15

Lys

<210> SEQ ID NO 75
<211> LENGTH: 16
<212> TYPE: PRT
<213> ORGANISM: Artificial Sequence
<220> FEATURE:
<223> OTHER INFORMATION: Artificial Antimicrobial peptide

<400> SEQUENCE: 75

Lys Cys Val Arg Val Cys Arg Arg Arg Ala Cys Arg Arg Arg Cys Lys
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Artificial Antimicrobial peptide

<400> SEQUENCE: 76

Lys Cys Val Arg Val Cys Arg Arg Gly Phe Cys Asn Arg Arg Cys Lys
1               5                   10                  15

<210> SEQ ID NO 77
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 77

Gly Phe Cys Trp Tyr Val Cys Lys Asn Gly Tyr Cys Tyr Arg Arg Cys
1               5                   10                  15

Asn

<210> SEQ ID NO 78
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 78

Gly Phe Cys Trp Tyr Val Cys Arg Asn Gly Tyr Cys Tyr Arg Arg Cys
1               5                   10                  15

Asn

<210> SEQ ID NO 79
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 79

Gly Phe Cys Trp Tyr Val Cys Arg Asn Gly Tyr Cys His Arg Arg Cys
1               5                   10                  15

Asn

<210> SEQ ID NO 80
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 80

Gly Phe Cys Trp Tyr Val Cys Tyr Arg Gly Ile Cys His Arg Arg Cys
1               5                   10                  15

Asn

<210> SEQ ID NO 81
<211> LENGTH: 16
<212> TYPE: PRT
<213> ORGANISM: Artificial Sequence
<220> FEATURE:
<223> OTHER INFORMATION: Artificial Antimicrobial peptide

<400> SEQUENCE: 81

Lys Cys Val Arg Val Cys Arg Arg Gly Phe Cys Asn Arg Arg Cys Lys
1               5                   10                  15

<210> SEQ ID NO 82
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 82

Gly Phe Cys Arg Tyr Val Cys Tyr Arg Gly Ile Cys Arg Arg Arg Cys
1               5                   10                  15

Asn

<210> SEQ ID NO 83
<211> LENGTH: 17

```
<212> TYPE: PRT
<213> ORGANISM: Artificial Sequence
<220> FEATURE:
<223> OTHER INFORMATION: Artificial Antimicrobial peptide

<400> SEQUENCE: 83

Lys Phe Cys Val Asn Val Cys Arg Asn Gly Ile Cys Arg Arg Arg Cys
1               5                   10                  15

Lys

<210> SEQ ID NO 84
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 84

Gly Val Cys Val Asn Val Cys Arg Arg Arg Phe Cys His Arg Arg Cys
1               5                   10                  15

Asn

<210> SEQ ID NO 85
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 85

Lys Lys Val Cys Val Asn Val Cys Lys Gln Gly Ile Cys His Lys Arg
1               5                   10                  15

Cys Lys

<210> SEQ ID NO 86
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 86

Lys Lys Val Cys Val Asn Val Cys Arg Gln Gly Ile Cys His Arg Arg
1               5                   10                  15

Cys Lys

<210> SEQ ID NO 87
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 87

Gly Phe Cys Arg Tyr Val Cys Arg Arg Gly Ile Cys Arg Arg Arg Cys
1               5                   10                  15

Asn

<210> SEQ ID NO 88
<211> LENGTH: 17
<212> TYPE: PRT
<213> ORGANISM: Artificial Sequence
<220> FEATURE:
<223> OTHER INFORMATION: Artificial Antimicrobial peptide
```

```
<400> SEQUENCE: 88

Lys Phe Cys Val Asn Val Cys Tyr Arg Gly Ile Cys Arg Arg Arg Cys
1               5                   10                  15
Lys

<210> SEQ ID NO 89
<211> LENGTH: 16
<212> TYPE: PRT
<213> ORGANISM: Artificial Sequence
<220> FEATURE:
<223> OTHER INFORMATION: Artificial Antimicrobial peptide

<400> SEQUENCE: 89

Lys Cys Arg Arg Val Cys Arg Arg Gly Phe Cys Tyr Val Val Cys Asn
1               5                   10                  15

<210> SEQ ID NO 90
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 90

Gly His Cys His His Val Cys Arg Arg His Cys His Arg Arg Cys
1               5                   10                  15
Asn

<210> SEQ ID NO 91
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 91

Gly Phe Cys Trp Tyr Val Cys Tyr Arg Gly Phe Cys Tyr Arg Arg Cys
1               5                   10                  15
Asn

<210> SEQ ID NO 92
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 92

Arg Gly Gly Arg Leu Cys Tyr Cys Arg Arg Phe Cys Val Cys Val
1               5                   10                  15
Gly Arg

<210> SEQ ID NO 93
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 93

Arg Arg Trp Cys Phe Arg Val Cys Tyr Arg Gly Phe Cys Tyr Arg Lys
1               5                   10                  15
```

Cys Arg

<210> SEQ ID NO 94
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 94

Gly Phe Cys Trp Tyr Val Cys Arg Arg Arg Phe Cys Tyr Arg Arg Cys
1               5                   10                  15

Asn

<210> SEQ ID NO 95
<211> LENGTH: 17
<212> TYPE: PRT
<213> ORGANISM: Artificial Sequence
<220> FEATURE:
<223> OTHER INFORMATION: Artificial Antimicrobial peptide

<400> SEQUENCE: 95

Gly Phe Cys Trp Tyr Val Cys Arg Arg Arg Phe Cys Tyr Arg Arg Cys
1               5                   10                  15

Asn

<210> SEQ ID NO 96
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 96

Lys Trp Cys Phe Arg Val Cys Tyr Gly Arg Ile Cys Tyr Arg Arg Cys
1               5                   10                  15

Arg Asp

<210> SEQ ID NO 97
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 97

Lys Arg Cys Phe Arg Val Cys Tyr Arg Gly Ile Cys Tyr Arg Arg Cys
1               5                   10                  15

Arg Asp

<210> SEQ ID NO 98
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 98

Lys Trp Cys Val Arg Val Cys Tyr Arg Gly Ile Cys Tyr Arg Arg Cys
1               5                   10                  15

Arg Asp

<210> SEQ ID NO 99

```
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 99

Lys Trp Cys Phe Phe Val Cys Tyr Arg Gly Ile Cys Tyr Arg Arg Cys
1               5                   10                  15

Arg Asp

<210> SEQ ID NO 100
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 100

Lys Trp Cys Phe Trp Val Cys Tyr Arg Gly Ile Cys Tyr Arg Arg Cys
1               5                   10                  15

Arg Asp

<210> SEQ ID NO 101
<211> LENGTH: 19
<212> TYPE: PRT
<213> ORGANISM: Artificial Sequence
<220> FEATURE:
<223> OTHER INFORMATION: Artificial Antimicrobial peptide

<400> SEQUENCE: 101

Lys Trp Cys Phe Arg Val Tyr Cys Tyr Arg Gly Ile Cys Tyr Arg Arg
1               5                   10                  15

Cys Arg Asp

<210> SEQ ID NO 102
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 102

Lys Trp Cys Phe Arg Ala Cys Tyr Arg Gly Ile Cys Tyr Arg Arg Cys
1               5                   10                  15

Arg Asp

<210> SEQ ID NO 103
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 103

Lys Trp Cys Phe Arg Val Cys Lys Arg Gly Ile Cys Tyr Arg Arg Cys
1               5                   10                  15

Arg Asp

<210> SEQ ID NO 104
<211> LENGTH: 18
<212> TYPE: PRT
<213> ORGANISM: Artificial Sequence
<220> FEATURE:
```

```
<223> OTHER INFORMATION: Artificial Antimicrobial peptide

<400> SEQUENCE: 104

Lys Trp Cys Phe Arg Val Cys Tyr Phe Gly Ile Cys Tyr Arg Arg Cys
1               5                   10                  15

Arg Asp

<210> SEQ ID NO 105
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 105

Lys Trp Cys Phe Arg Val Cys Tyr Arg Gly Ile Cys Tyr Arg Arg Cys
1               5                   10                  15

Arg Asn

<210> SEQ ID NO 106
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 106

Lys Trp Cys Trp Arg Val Cys Tyr Arg Gly Ile Cys Tyr Arg Arg Cys
1               5                   10                  15

Arg Asp

<210> SEQ ID NO 107
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 107

Lys Trp Cys Phe Arg Val Cys Trp Arg Gly Ile Cys Tyr Arg Arg Cys
1               5                   10                  15

Arg Asp

<210> SEQ ID NO 108
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 108

Lys Trp Cys Phe Arg Val Cys Tyr Gly Gly Ile Cys Tyr Arg Arg Cys
1               5                   10                  15

Arg Asp

<210> SEQ ID NO 109
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 109
```

Lys Trp Cys Phe Arg Val Cys Tyr Arg Arg Ile Cys Tyr Arg Arg Cys
1               5                   10                  15

Arg Asp

<210> SEQ ID NO 110
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 110

Lys Trp Cys Phe Arg Val Cys Tyr Arg Gly Tyr Cys Tyr Arg Arg Cys
1               5                   10                  15

Arg Asp

<210> SEQ ID NO 111
<211> LENGTH: 19
<212> TYPE: PRT
<213> ORGANISM: Artificial Sequence
<220> FEATURE:
<223> OTHER INFORMATION: Artificial Antimicrobial peptide

<400> SEQUENCE: 111

Lys Trp Cys Phe Arg Val Cys Tyr Arg Gly Ile Cys Arg Tyr Arg Arg
1               5                   10                  15

Cys Arg Asp

<210> SEQ ID NO 112
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 112

Lys Trp Cys Phe Arg Val Cys Tyr Arg Gly Ile Cys Tyr Arg Arg Cys
1               5                   10                  15

Lys Asp

<210> SEQ ID NO 113
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 113

Lys Trp Cys Phe Arg Val Cys Tyr Arg Gly Ile Cys Tyr Arg Arg Cys
1               5                   10                  15

Ala Asp

<210> SEQ ID NO 114
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 114

Lys Trp Cys Phe Arg Val Cys Tyr Arg Gly Ile Cys Tyr Arg Arg Cys
1               5                   10                  15

Arg Arg

```
<210> SEQ ID NO 115
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 115

Gly Trp Cys Phe Arg Val Cys Tyr Arg Gly Ile Cys Tyr Arg Arg Cys
1               5                   10                  15

Asn Asp

<210> SEQ ID NO 116
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 116

Lys Trp Cys Phe Tyr Val Cys Tyr Arg Gly Ile Cys Tyr Arg Arg Cys
1               5                   10                  15

Asn Asp

<210> SEQ ID NO 117
<211> LENGTH: 18
<212> TYPE: PRT
<213> ORGANISM: Artificial Sequence
<220> FEATURE:
<223> OTHER INFORMATION: Artificial Antimicrobial peptide

<400> SEQUENCE: 117

Gly Trp Cys Phe Tyr Val Cys Tyr Arg Gly Ile Cys Tyr Arg Arg Cys
1               5                   10                  15

Arg Asp
```